United States Patent [19]
Spruce et al.

[11] Patent Number: 5,968,824
[45] Date of Patent: *Oct. 19, 1999

[54] AGENTS FOR INDUCING APOPTOSIS AND APPLICATIONS OF SAID AGENTS IN THERAPY

[76] Inventors: Barbara Ann Spruce, Annat Cottage, Rait, Perthshire PH2 7SB; Alan Prescott, 13 Bankton Park, Kingskettle, Fife KY15 7PY; Angelika Bottger, 6 Bridge Street, Newport-on-tay DD6 8JJ; Deborah Ann Dewar, 22 North Street, Dundee DD1 7RR, all of United Kingdom

[*] Notice: This patent issued on a continued prosecution application filed under 37 CFR 1.53(d), and is subject to the twenty year patent term provisions of 35 U.S.C. 154(a)(2).

[21] Appl. No.: 08/793,490

[22] PCT Filed: Aug. 30, 1995

[86] PCT No.: PCT/GB95/02037

§ 371 Date: Apr. 28, 1997

§ 102(e) Date: Apr. 28, 1997

[87] PCT Pub. No.: WO96/06863

PCT Pub. Date: Mar. 7, 1996

[30] Foreign Application Priority Data

Aug. 30, 1994 [GB] United Kingdom .................... 9417444
Sep. 23, 1994 [GB] United Kingdom .................... 9419285

[51] Int. Cl.$^6$ .......................... A61K 31/40; A61K 31/44; C12N 1/00
[52] U.S. Cl. .......................... 435/375; 424/427; 427/2.24; 435/377; 514/279; 514/408; 514/912; 514/954
[58] Field of Search .................................. 514/408, 279, 514/912, 954; 435/375, 377; 427/2.24; 930/DIG. 740, DIG. 741, DIG. 742; 424/427

[56] References Cited

PUBLICATIONS

Chemical Abstracts, 115, 675s, 1991.
Zagon, Endogenous opiod systems regulate growth of neural tumor cells in culture, *Brain Res* 490 (1989) 14–25.
Bottger, Comprehensive epitope analysis of monoclonal anti–proenkephalin antibodies using phage display libraries and synthetic peptides: etc, *J Mol Biol 247* (1995) 932–46.
Hauser, Morphine inhibits purkinje cell survival and dendritic differentiation in organotypic cultures of the mouse cerebellum, *Exp Neurology 130* (1994) 95–105.
Meriney, Morphine–induced delay of normal cell death in the avian ciliary ganglion, *Science 228* (1985) 1451–53.
Hughes, Identification of two related pentapeptides from the brain with potent opiate agonist activity, *Nature 258* (1975) 577–79.
Pert, Opiate receptor: demonstration in nervous tissue, *Science 179* (1973) 1011–14.
Martin, The effects of morphine—and nalorphine—like drugs in the nondependent and morphine—dependent chronic spinal dog, *J Pharm and Exp Therapeutics 197* (1976) 517–32.
Maneckjee, Opioids induce while nicotine suppresses apoptosis in human lung cancer cells, *Cell Growth & Differentiation 5* (1994) 1033–40.
Bottger, Proenkephalin is a nuclear protein responsive to growth arrest and differentiation signals, *J Cell Biol 130* (1995) 1251–62.
Fuchs, Morphine induces apoptosis in murine thymocytes in vivo but not in vitro: etc., *J Pharm and Exp Therapeutics 266* (1993) 417–23.
Meriney, Endogenous opioids modulate neuronal survival in the developing avian ciliary ganglion, *J Neuroscience 11* (1991) 3705–17.
Hollstein, p53 mutations in human cancers, *Science 253* (1991) 49–53.
Lu, Differential induction of transcriptionally active p53 following UV or ionizing radiation: etc., *Cell 75* (1993) 765–78.
Sonnenberg, Regulation of proenkephalin by Fos and Jun, *Science 246* (1989) 1622–25.
Zurawski, Activation of mouse T–helper cells induces abundant preproenkephalin mRNA synthesis, *Science 232* (1986) 772–775.
Vilijn, Cultured Astrocytes and neurons synthesize and secrete carboxypeptidase E, a neuropeptide–processing enzyme, *J Neurochemistry 53* (1989) 1487–93.
Spruce, A neuropeptide precursor in cerebellum: etc., *EMBO J 9* (1990) 1787–95.
Melner, The regulation of proenkephalin expression in a distinct population of glial cells, *EMBO J 9* (1990) 791–96.
Thompson, Cloning and pharmacological characterization of a rat mu opioid receptor, *Neuron 11* (1993) 903–13.
Meng, Cloning and pharmaacological characterization of a rat kappa opioid receptor, *Proc Natl Acad Sci 90* (1993) 9954–58.
Lord, Endogenous opioid peptides: multiple agonists and receptors, *Nature 267* (1977) 495–99.
Hauser: Morphine regulates DNA synthesis in rat cerebellar neuroblasts in vitro, *Developmental Brain Res 70* (1992) 291–97.

*Primary Examiner*—David Saunders
*Attorney, Agent, or Firm*—Luann Cserr

[57] ABSTRACT

Agents which modulate pathways of apoptotic induction or repression in which products of opioid peptide precursors genes participate, useful as inducers of apoptosis in cells and in tumor cells in particular, are disclosed. Methods of treatment employing such agents and pharmaceutical compositions containing them are also described.

6 Claims, 6 Drawing Sheets

Fig.4.

```
MARFLTLCTW  LLLLGPGLLA  TVRAECSQDC  ATCSYRLVRP  ADINFLACVM    50

ECEGKLPSLK  IWETCKELLQ  LSKPELPDQG  TSTLRENSKP  EESHLLAKRY   100

GGFMKRYGGF  MKKMDELYPM  EPEEEANGSE  ILAKRYGGFM  KKDAEEDDSL   150
     IV

ANSSDLLKEL  LETGDNRERS  HHQDGSDNEE  EVSKRYGGFM  RGLKRSPQLE   200
    I                        II         III

DEAKELQKRY  GGFMRRVGRP  EWWMDYQKRY  GGFLKRFAEA  LPSDEEGESY   250

SKEVPEMEKR  YGGFMRF                                          267
```

I      PE-14, PE-15, PE-16, PE-17, PE-18, PE-19, PE-23, PE-25

II     PE-13, PE-20, PE-21, PE-22, PE-24

III    PE-1

|  |  | CDR1 |  | CDR2 |
|---|---|---|---|---|
| PE14 | VQLQESGPELVKPGASVRISCKTSGYTFT | ENTLH | WVKQSHGKSLEWIG | GIHPKNGGTNYNQKFKG |
| PE16 | ----------------------------- | ----- | -------------- | ----------------- |
| PE17 | ----------------------------- | ----- | -------------- | -T--------------- |
| PE18 | -----------T-L--------------- | ----- | -------------- | ----------------- |
| PE19 | -------------T--------------- | ----- | -------------- | ----------------- |
| PE25 | -K-R------------------------- | ----- | -------------- | --------------RV- |
| PE15 | -K--------------------K------ | --M-- | -------------- | --N-N---LY-----V- |
| PE23 | -K--------Q-----------K------ | ---I- | -------------- | --N-N---R-S----QD |
| | | | | |
| PE20 | VQLQESGGGLVKPGGSLKLSCAASGFTFS | TYAMS | WVRQTPEKRLEWVA | TISSGGSYTYYPDSVKG |
| PE21 | --------------------------R-- | S---- | -------------- | ----------------- |
| PE22 | -K--------------------------- | S---- | -------------- | ---S-N----------- |
| PE24 | ----------------------------- | S---- | -------------- | ---S------------- |
| PE13 | -K----------------------F---- | S---C | ------N------- | -V--S-T----S-T--- |
| | | | | |
| PE1 | VQLQESGTVLARPGASVKTSCKASGYSFT | SYWMH | WVKQRPGQGLEWIG | AIYPGNSDTSYNQKFKG |
| | | | | |
| PE2 | VQLQESGAELVKPGASVKLSCKASGYTFT | RYYMY | WVKQRPGQGLEWIG | EINPSNGGTNFNEKFKS |

Fig.5. (Cont.)

```
                                                    CDR3
KATMTVDKSSSTAYMDFRSLTFDDSAVYYCVR                    GDGAY
-------------------------------                     -----
-------------------------------                     -----
-----T-------------------------                     -----
----------------E----------A---                     -----
--L-----------------E------A---                     -----
R--L----------------E------A---                     -----
--L----EL----------SE------A---                     -----
---PL--A---EV------SE----F-A---                     ---V-

RFTISRDNAKNTLYLQMSSLRSEDTAMYYCAR                    LYYDYD PYVMDY
-------------------------------T-                   ------ ------
-----M-------------------------V-                   ------ -----F
-----M-------------------------V-                   ------ ------
--------------I----------------V-                   ---S--G--A---

KAKLTAVTSASTAYMELSSLTNEDSAVYYCTR                    EGYTTGGDY

KATLTVDKSSSTAYMQLSSLTSEDSAVYYCTR                    GVVASMDY
```

AGENTS FOR INDUCING APOPTOSIS AND APPLICATIONS OF SAID AGENTS IN THERAPY

The present invention relates to the use of agents which modulate pathways in which products of so-called opioid peptide precursor genes participate in such a way as to induce cell apoptosis, in particular in tumour cells or lens cells, to methods of treatment employing such agents and to pharmaceutical compositions containing them.

The discovery of receptors within the brain which bind the opium derivative morphine (Pert and Snyder, 1973 Science 179, 1011–1014) preceded the isolation of two pentapeptides with potent opiate agonist activity in bioassay systems (Hughes et al., 1975, Nature, 258, 577–580). The pentapeptides, which differ only in their COOH— terminal amino acid, were named Met- and Leu-enkephalin to reflect their origin from brain. Peptides containing these sequences are termed opiate or opioid peptides. Enkephalins are widely distributed throughout the central nervous system in enkephalinergic neuronal networks, and also exist in the peripheral nervous system, for example in autonomic ganglia. Data, largely circumstantial, suggest wide-ranging involvement of endogenous opioids for example in the modulation of pain perception, in mood and behaviour, learning and memory, diverse neuroendocrine functions, immune regulation, and cardiovascular and respiratory function.

The observation that the opiate alkaloid nalorphine has a dual action in antagonising the analgesic effect of morphine but also acts as an analgesic in its own right, led to the suggestion that there may be several types of receptor which bind opiate compounds (Martin 1967 Pharmacol. Rev. 19, 463–521). Differential responses to a number of opiates in an animal model suggested three types of opiate receptor— mu, kappa, and sigma (Martin et al., 1976 J. Pharmacol. Exp. Ther. 197, 517–532.) Lord and colleagues (1977 Nature 267, 495–499) compared the activity of morphine and enkephalins in bioassay systems; the results indicated the existence of delta receptors, to which enkephalins bound predominantly, and mu receptors, to which morphine bound preferentially. Synthetic analogues subsequently supported the separation of opioid receptors into three main types— delta, kappa and mu—which has remained a pharmacological classification. Genes encoding these three main receptor types have now been cloned. Prototypic analogues which are selective agonists at the three main receptor types include DAMGO (Tyr-DAla-Gly-MePhe-Glyol) (mu); DPDPE (Tyr-DPen-Gly-Gly-Phe-DPen-OH) (delta); and for the kappa, U50,488. However, the selectivity of these compounds is dose dependent and all have the potential to cross-react with other receptor types (Goldstein 1987 Trends Pharm. Sci. 8, 456–459).

Sequencing of the cloned opioid receptor genes has revealed a substantial degree of amino acid homology between different receptor types (Meng et al., 1993 Proc. Natl. Acad. Sci U.S.A. 90, 9954–9958; Thompson et al., 1993 Neuron 11, 903–913; Evans et al, Science 1992 258, 1952–1955; Kieffer et al., Proc. Natl. Acad. Sci. U.S.A. 1992 89, 12048–12052); this explains the tendency of opioid receptor ligands, even those purported to be selective, to bind more than one type. Alignment of the sequences of the main receptor types with less closely related molecules such as the immunoglobulin superfamily member OBCAM (Schofield et al., EMBO J. 1989 8, 489–495) supports the reported opioid binding properties of the purified OBCAM molecule, and indicates the potential for additional opioid receptor ligands to bind this and other related receptor molecules. Furthermore, additional receptor families, in particular the somatostatin receptors, share close homology with the opioid receptors, and on the basis of these structural similarities (which are illustrated hereinafter in FIG. 1) would also be expected to bing opioid receptor ligands.

Opioid receptor subtypes based on differences in the binding profiles of natural and synthetic ligands have also been suggested, including mu1 and mu2 (Pasternak and Wood 1986 Life Sci. 38, 1889–1898) and kappa1 and kappa2 (Zukin et al., 1988 Proc. Natl. Acad. Sci. U.S.A. 85, 4061–4065). Tentative assignations of receptor subtypes to those cloned so far include kappa1 (Meng et al., 1993 as above) and mu2 (Thompson et al., 1993 as above). Delta opioid receptors independently cloned from the same cell line, found to have a sequence difference in one region, may represent different delta receptor subtypes which co-exist in the same cell (Evans et al., 1992; Kieffer et al., 1992, as above). Based on pharmacological data, further subdivisions of receptor subtypes, and additional main receptor types including sigma, epsilon and zeta have also been proposed.

It is clear that until the entire opioid receptor gene family has been cloned, and tested against all the available pharmacological compounds, the assignation of each cloned molecule to its putative pharmacological counterpart must remain provisional. Even then, it remains possible that the same cloned molecule could confer different pharmacological profiles by for example variable post-translational modifications or heterooloigomeric complexing with other opioid, or even non-opioid, receptors. It may be that when more members of the opioid receptor family have been cloned, some revision of the classification will be necessary. That having been said, in the context of the present application, the presently accepted classification will be applied.

Natural ligands for the main receptor types are in general less selective than many of the synthetic analogues; however, they do exhibit preferences for binding. The pentapeptides Met- and Leu-enkephalin preferentially bind delta receptors. The Leu-enkephalin-containing peptide dynorphin predominantly binds the kappa receptor type. Mu receptor ligands include the opioid peptide β-endorphin, metorphamide, and some dynorphin-related peptides. The full profile of natural ligands for each of these receptors is unknown and it is likely that alternative products of each of the opioid precursors (see below) bind different receptor types. Although the opiate alkaloid morphine principally binds the mu receptor, peripheral administration of morphine induces release of enkephalins which will then interact with delta receptors (Bertolucci et al., 1992 Soc. Neurosci. Abstr. 1368).

Opioid peptides are derived by proteolytic cleavage from much larger precursor molecules. Three opioid precursor genes exist. Proenkephalin gives rise to "free" Met- and Leu-enkephalin. Proopiomelanocortin is cleaved to the Met-enkephalin-containing peptide β-endorphin, and prodynorphin (or proenkephalin B) to the Leu-enkephalin-containing peptide dynorphin. In addition, all three precursors have the potential to be differentially cleaved into multiple extended enkephalin and non-enkephalin-containing peptides, the functions of which are largely unknown; however, in some cases it has been shown that extended enkephalin-containing peptides have enhanced opiate activity.

Traditional thinking has viewed opioid, and indeed all neuropeptide, precursors as biologically inert, whose only destiny is to be cleaved into the bioactive peptides which are then released from the cell. However, there is a growing body of evidence that proenkephalin exists largely independently of free enkephalin peptides in a number of tissues and cell types including astrocytes (Melner et al., 1990 EMBO J. 9, 791–796; Spruce et al., 1990 EMBO J. 9, 1787–1795) and is released from these cells in an unprocessed form (Batter et al., 1991 Brain Res. 563, 28–32). Proenkephalin also exists in lymphocytes (Roth et al., 1989 FASEB J. 3, 2401–2407; Rosen et al., 1989 J. Immunol. 143, 3703–3707), fibroblasts (Rosen et al., 1990 Biochem. Biophys. Res. Comm. 171, 722–728), and gonadal tissue (Garrett et al., 1990 Mol. Endocrinol. 4, 108–118; Kew et al., 1990 Proc. Natl. Acad. Sci. U.S.A. 87, 9143–9147). There is evidence in some cases that processing enzymes are co-released along with the unprocessed precursor which suggests that extracellular cleavage may occur (Vilijn et al., 1989 J. Neurochem. 53, 1487–1493). Even if biological activity is signalled through binding of the small peptide products to cell surface receptors, the regulation of this activity may be mediated through the precursor, and it is also possible that the unprocessed precursor has an additional intracellular role of its own.

The discovery that proenkephalin exists in many non-neural cell types raised the question of a more generalised, possibly more fundamental, function. In addition to its expression in the mature cell types mentioned above, the proenkephalin gene is also expressed transiently in developing non-neural as well as neural tissues (Keshet et al., 1989 EMBO J. 8, 2917–2923). Additional studies have addressed a possible connection between opioid peptides and alkaloids and cell proliferation and differentiation (Hauser et al., 1989 J. Comp. Neurol. 281, 13–22; Hauser 1992 Dev. Brain Res. 70, 291–297). The maintained expression of proenkephalin in cell types which remain competent to divide throughout life (see above), and its upregulation upon mitogenic activation of T helper cells (Zurawski et al., 1986 Science 232, 772–775), suggests a relationship between products of the proenkephalin gene and the proliferative status of the cell, or the state of readiness to divide. However, this connection is not a universal one since proenkephalin is also expressed in for example post-mitotic neurons following epileptic seizure, and closely follows the induction of Fos and Jun which are known transcription factors for the gene (Sonnenberg et al., 1990 Science 246, 1622–1625.) It is possible therefore that in this case proenkephalin gene products may be acting as intracellular or autocrine stress response molecules, which would be an extension of previous data suggesting that endogenous opioids may be stress response molecules (Olson 1987 Peptides 8, 1135–1164).

Kerr, Wyllie and Currie (1972 Brit. J. Cancer 25, 239–257) coined the term "apoptosis" to describe a morphologically distinct process of controlled cell death which balances the process of cell production by mitosis. This type of active cell elimination has been proposed to be an important regulator of animal cell populations (Kerr et al., 1972, as above), and may even be an intrinsic programme in all cells (Raff 1992 Nature 356, 397–400). A molecular connection between the control of cell production and cell elimination is now established. Molecules with established regulatory roles in proliferation control such as c-myc and p53 are also implicated in pathways mediating apoptotic cell death. C-myc, a molecule which promotes cell proliferation in a favourable "growth environment", promotes cell death instead when levels of exogenous survival factors are low (Evan et al., 1992 Cell 63, 119–125; Harrington et al., 1994 EMBO J. 13, 3286–3295). Wyllie and colleagues (Kerr et al., 1972, as above) proposed that the regression of malignant tumours might be due to spontaneous or therapeutically-induced apoptosis. Evan (Harrington et al., 1994 as above) has suggested that the coupling of the mitogenic and apoptotic pathways, through the dual action of c-myc, may be an important safeguard against tumour progression, so that a hyperproliferating cell population will apoptose when levels of exogenous survival factors become limiting.

An additional safeguard against the development of tumours is provided by p53, since animals lacking both copies of their p53 gene have a very high incidence of tumours (Donehower et al., 1992 Nature 356, 215–221). p53 has been shown to be necessary for etoposide and radiation induced apoptosis in thymocytes (Clarke et al., Nature 362, 849–852; Lowe et al., 1993 Nature 362, 847–849), which therefore links it to a DNA damage dependent pathway to apoptosis. Lu and Lane (Cell 1993 75, 765–778) have shown induction of transcriptionally active p53 which precedes the onset of apoptosis in irradiated cells. Lane has proposed that p53 acts as the "guardian of the genome". The repair of rectifiable damage is facilitated by the induction of growth arrest by p53, whereas cells with non-rectifiable damage, containing potentially oncogenic mutations, are eliminated through a p53 dependent pathway to apoptosis. Oren and colleagues (Yonish-Rouach et al., Nature 1991 352, 345–347) showed induction of apoptosis by transfected p53 in myeloid leukaemia cells, which is prevented by interleukin-6. Thus, p53 dependent pathways to apoptosis may also be integrated with survival signals from the outside of the cell.

Raff and colleagues (1992 Nature 356, 397–400; Raff et al., 1993 Science 262, 695–699) have proposed that all mammalian cells may be programmed to die by default in the absence of continuous signalling from neighbouring cells. Evidence indicates that a variety of external stimuli promote survival. These include soluble endocrine factors which originate at a distance (as in the support of adrenocortical cell survival by pituitary-derived adrenocorticotrophic hormone; Wyllie et al., 1973 J. Pathol. 111, 85–94); paracrine factors which originate from neighbouring cells of a different type (as in the promotion of oligodendrocyte survival; Barres et al., 1992 Cell 70, 31–46); or autocrine factors from neighbouring cells of the same type (as exemplified in lens cells and chondrocytes; Ishizaki et al., 1993 J. Cell Biol, 121, 899–908; Ishizaki et al., 1994 J. Cell Biol, 126, 1069–1077). Nondiffusible signals are also recognised to promote survival such as those delivered by cell adhesion molecules (Bates et al., 1994 J. Cell Biol, 125, 403–415), contact with the extracellular matrix (Meredith et al., 1993 Mol. Biol. Cell 4, 953–961), or by tight junctions and desmosomes (Ning and Hahn, 1994 J. Cell. Physiol. 160, 249–254). It is likely that a combination of different types of signals is required to suppress the death programme.

The possession of a cell-intrinsic death programme which is suppressed by signals from the surrounding environment prevents cells from surviving as single cells when isolated from their neighbours. The evolutionary advantage of this would be that cells which become misplaced during development are eliminated; furthermore, since all cells are competing for limiting amounts of survival signals, only the fittest will survive (Raff, 1992, as above). However, the acquisition of a survival advantage which helps a cell overcome its need for signals from its neighbours would favour tumour progression, since a hyperproliferating cell population would continue to expand even when it began to outstrip its supply of survival factors; furthermore, metastatic tumour cells would be tolerated in an alien environment and would fail to be eliminated (Raff, 1992). The acquisition of a survival advantage which prevented a single cell from activating its suicide programme in response to levels of genetic damage associated with common environmental insults could theoretically be an initiating event in oncogenesis since it would favour the persistence of potentially tumorigenic mutations. A particularly potent genetic event would be one which promoted the degree of genetic damage as well as inhibited the suicide response after exposure to environmental genotoxins. No such gene candidate or pathway has yet been identified; the present invention addresses a candidate pathway.

Survival autonomy could theoretically be acquired by a number of potential mechanisms, for example: through mutational activation of autocrine survival factors (as discussed above) or survival factor receptors: by deregulation of intracellular survival molecules such as Bcl-2 (see later); or if survival pathways normally activated through cell-cell contact became decoupled from these signals. Inappropriate activation of survival pathways in any of these ways, which might lead to override of the intrinsic death programme, could in theory promote tumorigenesis at early and late stages. A particularly potent oncogenic pathway would be one which both promoted and tolerated genetic damage and helped a cell overcome its need for extracellular survival signals. The present invention addresses such a "pathway", or more likely coupled pathways, in which opioid-like molecules participate. Collectively, the data indicate that such a pathway is dysregulated in several tumour cell types, which have become dependent on it for survival; a therapeutic opportunity is therefore provided. Furthermore, since inappropriate activation of such a pathway has the potential to be involved at multiple stages of the oncogenic process, there is a strong possibility that the majority of tumours will harbour a mutation which affects this pathway.

The first gene to be identified which implicated the repression of apoptosis in tumorigenesis was the bcl-2 gene. Bcl-2, located at the t(14:18) chromosomal translocation breakpoint in follicular lymphomas (Bakshi et al., 1985 Cell 41, 899–906) was the first oncogene to be identified which promotes cell survival rather than proliferation. B lymphoid tumours develop after a long latency in transgenic animals overexpressing bcl-2 in the lymphoid lineage (Strasser et al., 1993 Oncogene 8, 1–9) and bcl-2 cooperates with c-myc to immortalise pre-B cells (Vaux et al., 1988 Nature 335, 440–442). However, in the majority of tumours bcl-2 is not deregulated. "Loss-of-function" mutations in the p53 tumour suppressor gene repress the apoptotic response to genetic damage and occur commonly in human cancer (Hollstein et al., 1991 Science 253 49–53)*; however, approximately 50% of human tumours possess normal p53 function. Thus, additional pathways or molecules which inappropriately repress apoptosis in human tumours remain to be identified.

There are published reports that pathways which include opioid-like molecules participate in regulating the equilibrium between cell death and survival; however, the data are conflicting. Morphine promotes survival in the developing avian ciliary ganglion (Meriney et al., 1985 Science 228, 1451–1453). The involvement of endogenous opioid pathways in the same system has been established (Meriney et al., 1991 J. Neurosci. 11, 3705–3717). In contrast, morphine inhibits cell survival in the developing cerebellum (Hauser et al., 1994 Exp. Neurol. 130, 95–105) and induces apoptosis in thymocytes (Fuchs and Pruett, 1993 J. Pharmacol. Exp. Ther. 266, 417–423).

The present invention presents evidence that pathways in which opioid-like molecules participate can promote or repress apoptosis, which would be a possible explanation for apparently opposing effects of morphine. Further entirely novel findings are that the regulation of the death/life equilibrium is at least partly controlled through one of the opioid precursor molecules, proenkephalin, and that one or more pathways with which this molecule interacts have become dysregulated during the transformation process. This has led to a greater dependence of tumour compared with non-tumour cells on opioid-like pathways for survival which therefore provides a therapeutic opportunity. Biological data has now been obtained which implicate the widespread involvement of opioid-like pathways in the oncogenic process. Furthermore, therapeutic agents and conditions for their optimal activity have been identified.

In a series of investigations summarised below, it has been found that:

In transformed cells, proenkephalin, and/or its proteolytic products, act as extracellular and/or cell surface membrane bound factors which modulate cell survival a) upon deprivation of exogenous survival factors, and b) following genotoxic injury and/or stress when exogenous survival factors are non-limiting. The receptor(s) to which these factor(s) bind, which are most likely to exist on the cell surface, are related, or possibly identical, to one or more members of the opioid receptor family.

Opioid-like receptor types or subtypes can mediate survival or death; receptor(s) which mediate death appear to be coupled to those which mediate survival. Natural ligands for these receptors are likely to be products of the opioid precursor genes, although natural ligands could include cytokines which mimic their effects.

Tumour cells are more sensitive to antagonism of opioid-like receptor-mediated survival, and to stimulation of opioid-like receptor-mediated death, than non-transformed cells. The induction of cell cycle arrest enhances the sensitivity of tumour cells to these manipulations. (Enhanced sensitivity of tumour cells to these manipulations is induced by their synchronisation within the cell cycle.)

Cytoplasmic proenkephalin and/or its proteolytic products act as general repressors of apoptosis. Agents which, if coupled to appropriate internalisation agents, would antagonise cytoplasmic proenkephalin would therefore be of use in the induction of apoptosis in non-transformed as well as transformed cells, particularly in combination with sublethal doses of known apoptosis-inducing agents.

The repression of apoptosis mediated through cytoplasmic proenkephalin is activated at high cell density predominantly by nondiffusable factors. Inhibition of proenkephalin or its products as described above would therefore be potentiated if agents were used in combination for example with neutralising antibodies to integrins (such as the antibody 23C6- Bates et al., J. Cell Biol. 125, 403–415) to reduce exogenous survival signalling and simulate low density.

Proenkephalin targetted to the cell nucleus induces apoptotic death, which is inhibited by the overexpresssion of large T antigen and is at least partly mediated through p53. Tumours which retain wild-type p53 function are therefore a particular target for apoptosis induction by agents which increase the levels of proenkephalin, or its derivatives, within the nucleus or which mimic the function of nuclear proenkephalin or its derivatives.

Following on from these findings, the invention provides a means of inducing apoptosis in cells which comprises modifying a biological pathway of a cell in which a product of an opioid precursor gene participates in such a way that the cell is caused to apoptose. Modification of the pathway is suitably effected by adminstration of an appropriate agent.

In particular, the present invention provides an agent for use in inducing apoptosis in cells, said agent comprising:

1) an agent able to neutralise proenkephalin or its proteolytic derivatives;
2) an agent which increases the level of nuclear proenkephalin and/or its derivatives, or which activates or mimics them; or
3) an agent which acts as an antagonist at receptor(s) related or identical to the delta opioid receptor, or an agent which acts as an agonist at receptor(s) related or identical to the kappa opioid receptor.

A subset of such agents are agents able to neutralise proenkephalin or its proteolytic derivatives, or an agent which acts as an antagonist at receptor(s) related or identical to the delta opioid receptor, or an agent which acts as an agonist at receptor(s) related or identical to the kappa opioid receptor.

In the case of (1) above, the agent may be administered to the cell surface whereupon the survival effects of extracellular and/or cell surface membrane bound proenkephalin or its proteolytic derivatives is neutralised causing the cell to become apoptotic. Alternatively, an agent able to neutralise proenkephalin or its proteolytic derivatives may be coupled to an internalisation peptide and a cytoplasmic anchor. Such an assembly will remain in the cytoplasm of the cell, antagonizing cytoplasmic proenkephalin and/or its proteolytic products and thus neutralising the apoptosis repressor effect of these molecules.

As used herein, the expression "internalisation peptide" relates to peptides which can facilitate transport of a molecule through a cell surface membrane. Examples of suitable internalisation peptides are those described in WO 91/18981 and sold by Appligene under the trade name "PENETRATIN". The expression "cytoplasmic anchor" relates to molecules such as peptides which effectively bind to cytoplasmic structures such as the endoplasmic reticulum or cell membranes and thereby prevent migration of any molecule to which they are attached into the nucleus or indeed out of the cell. An example of such an anchor is a hydrophobic leader sequence.

In the case of (2) above, the agent may be coupled to an internalisation peptide as described above or to a recognised nuclear localisation signal (NLS) to ensure nuclear concentration of the agent.

Non-transformed cells are less susceptible than transformed cells to the above-mentioned agents even in an environment in which exogenous survival factors are compromised. Exogenous survival factors are supplied to cells grown in tissue culture by the provision of, for example, fetal calf serum; such factors would be provided in vivo either from a distance and delivered via blood or lymph, in an endocrine fashion, or from neighbouring cells of a different type, in a paracrine fashion. In contrast, malignant tumour cells are susceptible to these agents, and the susceptibility is enhanced when exogenous survival factors are limiting or when cells have received a genotoxic or stress injury. The apoptotic effect is also enhanced by administration of agents of the invention following the induction of cell cycle arrest with appropriate agents.

Therefore, tumour cells rely for their survival on pathway (s) which depend on opioid-like molecules and/or their receptors. (One explanation might be that opioid-like receptors which promote survival are constitutively active in tumour cells so that alternative parallel survival pathways, either autocrine or intracellular, have become downregulated to compensate for the cell's perception of an inappropriate survival signal.) Hence the agents are particularly useful in the treatment of diseases such as cancer and this application, together with pharmaceutical compositions containing said agents form a further aspect of the invention.

The agents of the present invention have the advantage of promoting apoptosis of tumour cells with less or no effect against "normal" mature cell types which may lead to tumour regression without being lethal to the patient. A greater differential effect on proliferating compared with non-proliferating cell populations would also be revealed by combining genotoxic and/or cell cycle arrest (synchronisation) agents, with agents of the invention.

Other cells which depend on opioid-like factors or their receptors for survival include cells within the lens of the eye. There are occasions when it would be helpful to induce apoptosis in such cells, for example after surgical cataract removal, where the elimination of residual lens capsule cells is desirable to prevent future regrowth and opacification of the implant. Consequently the use of the apoptosis inducing agents in this mode of therapy forms a further aspect of the invention as will be explained in more detail hereinafter.

Examples of agents which neutralise proenkephalin or its proteolytic derivatives include neutralising monoclonal antibodies to proenkephalin or its proteolytic derivatives, and fragments of said antibodies which include the binding domain, as well as active derivatives of said antibodies and fragments and allelic forms.

Partial information concerning the generation and characterisation of a subset of anti-proenkephalin monoclonal antibodies, specifically PE-1, PE-2, PE-18 and PE-25 is described in J. Biol. Chem. (1988) 263, 36, 19788–19795, and EMBO J. (1990) 9, 6, 1787–1795. A further eleven antibodies (PE-13, PE-14, PE-15, PE-16, PE-17, PE-19, PE-20, PE-21, PE-22, PE-23, PE-24) have been raised to the same fusion protein as PE-18 and PE-25 as described in EMBO J. 1990 9, 1787. It was found that a clear serum response could only be obtained after the animals had received a total of from 6 to 8 injections over a period of from 12 to 18 months. These fifteen antibodies recognise several epitopes which have been mapped using a phage library incorporating randomly generated sequences and also using synthetic peptides. Core sequences of the epitopes recognised by the PE antibodies, and the antibody groups which are directed to these have been published (Bottger et al., J. Mol. Biol. (1995) 247, 932–946). The phage display data also indicate some influence of flanking sequences which points to an additional contribution of the higher order structure of the protein to epitope recognition.

Five hybridoma lines generating representative examples of the above-mentioned antibodies were deposited at the European Collection for Animal Cell Cultures (ECACC at the PHLS Centre for Applied Microbiology and Research, Salisbury, Wiltshire) on 11th October 1993. The lines, PE-1, PE-2, PE-13, PE-14, and PE-24 have the following accession numbers: 93101213, 93101215, 93101232, 93101234 and 93101254, and form a further part of the invention.

The variable domains of the heavy chain anti-proenkephalin immunoglobulin genes have been cloned also as described below; these sequences are shown in FIG. 5. Antibodies or binding antibody fragments which recognise any of the epitopes substantially as set out in FIG. 4 and/or include the variable domains as set out in FIG. 5 or which are substantially homologous to those set out in FIG. 5 form part of the invention. The heavy chain component of any variable domain contributes much of the specificity to antibody binding. Suitably homologous sequences have at least 60%, preferably at least 90% homology.

The above-described antibodies, since they are of use in therapy, may be "humanised" using for recombinant DNA technology. Specifically, the tail region of a non-human antibody in accordance with the invention may be exchanged for that of a human antibody. For a more complete humanisation, the framework regions of the non-human antibody may be exchanged for human framework regions as is known in the art. These exchange processes may be carried out at the DNA level using recombinant techniques. Such procedures have the effect of increasing the characteristic features of the antibodies which are specific to human proteins and thus reduces the possibility of harmful hypersensitivity reactions occurring.

Neutralising anti-proenkephalin antibodies would also be of use to inhibit cytoplasmic proenkephalin and thereby induce apoptosis in a range of non-transformed as well as transformed cell types; such an approach could be useful in the treatment of for example autoimmune diseases which arise from a defect in apoptosis. To promote translocation across the cell membrane the antibodies would be coupled to a chimeric peptide consisting of an internalisation peptide such as "PENETRATIN"™ (amino acid sequence R-Q-I-K-I-W-F-Q-N-R-R-M-K-W-K-K) with or without a cytoplasmic anchor sequence to ensure retention in the cytoplasm. A suitable cytoplasmic anchor would be a hydrophobic leader "signal" sequence to dock the agent onto the endoplasmic reticulum membrane, where intracellular proenkephalin is localised. Translocation into the lumen of the endoplasmic reticulum, and thence to the secretory pathway, usually occurs co-translaionally. Thus an appended signal peptide sequence is unlikely to direct the agent into the secretory pathway. Such an approach could also be used for other antagonistic agents.

Other agents which are of use to induce apoptosis are those which increase levels of proenkephalin and/or its proteolytic derivatives in the cell nucleus, or agents which activate or mimic nuclear proenkephalin or its derivatives. Examples of such agents include proenkephalin and its proteolytic derivatives as well as active fragments thereof. These may be derived from natural sources or synthesised for example using recombinant DNA technology. Agents which mimic nuclear proenkephalin include opioid analogues or anti-idiotypic antibodies as well as other mimetics (see below). Such agents may be coupled to an internalisation peptide such as "PENETRATIN"™, to promote translocation across the cell membrane and accumulation in the nucleus. The agent may also be coupled to a recognised nuclear localisaion signal (NLS) such as the NLS of SV40 large T antigen in order to ensure concentration of the agent in the nucleus. Preferably the agent is coupled to a chimera consisting of both an internalisation peptide and an NLS.

The designing of mimetics to a pharmaceutically active compound is a known approach to the development of pharmaceuticals based on a "lead" compound. This might be desirable where the active compound is difficult or expensive to synthesise or where it is unsuitable for a particular method of administration, eg peptides are unsuitable active agents for oral compositions as they tend to be quickly degraded by proteases in the alimentary canal. Mimetic design, synthesis and testing is generally used to avoid randomly screening large number of molecules for a target property.

There are several steps commonly taken in the design of a mimetic from a compound having a given target property. Firstly, the particular parts of the compound that are critical and/or important in determining the target property are determined. In the case of a peptide, this can be done by systematically varying the amino acid residues in the peptide, eg by substituting each residue in turn. These parts or residues constituting the active region of the compound are known as its "pharmacophore".

Once the pharmacophore has been found, its structure is modelled to according its physical properties, eg stereochemistry, bonding, size and/or charge, using data from a range of sources, eg spectroscopic techniques, X-ray diffraction data and NMR. Computational analysis, similarity mapping (which models the charge and/or volume of a pharmacophore, rather than the bonding between atoms) and other techniques can be used in this modelling process.

In a variant of this approach, the three-dimensional structure of the ligand and its binding partner are modelled. This can be especially useful where the ligand and/or binding partner change conformation on binding, allowing the model to take account of this the design of the mimetic.

A template molecule is then selected onto which chemical groups which mimic the pharmacophore can be grafted. The template molecule and the chemical groups grafted on to it can conveniently be selected so that the mimetic is easy to synthesise, is likely to be pharmacologically acceptable, and does not degrade in vivo, while retaining the biological activity of the lead compound. The mimetic or mimetics found by this approach can then be screened to see whether they have the target property, or to what extent they exhibit it. Further optimisation or modification can then be carried out to arrive at one or more final mimetics for in vivo or clinical testing.

Additional agents which are useful in the context of the present invention are those known from existing classifications as delta opioid receptor antagonists or kappa opioid receptor agonists. As used herein the references to agents which are delta opioid receptor antagonists includes agents which, when tested against classical opioid receptor types, preferentially antagonise the activity of delta opioid receptor (s), for example 4,8-methanobenzofuro[2,3-a]pyrido[4,3-b]carbazole-1,8a(9H)-diol,7-(cyclopropylmethyl)-5,6,7,8,14,14b-hexahydro, otherwise known as "naltrindole" (Chemical abstract number [111469-81-9] $C_{26}H_{26}N_2O_3 \cdot HCl$). Correspondingly, references to agents which are kappa opioid agonists include compounds which preferentially stimulate activity at kappa opioid receptor(s), such as trans-3,4-Dichloro-N-Methyl-N-(2-[1-pyrrolidinyl]cyclohexyl)benzene-acetamide, known as "U50488".

As described earlier, delta and kappa opioid receptor molecules are defined pharmacologically by the binding properties of selective ligands to them.

Other such agents which bind classical delta and kappa receptors might be determined by appropriate pharmacological tests as would be apparent to the skilled person.

However, a more meaningful test in biological terms of agents which would be candidate ligands at these or related receptors, such as the full profile of opioid receptor ligands, would employ the bioassays described hereinafter. These monitor apoptotic death as a biological end-point, in the way described, and would be performed at low cell density in the presence of low serum, genotoxic, cell cycle arrest (synchronisation), or stress-inducing agents.

The invention further provides an assay for determining agents which induce apoptosis in cells, which assay comprises administering an agent under test to cells at low cell density in the presence of low serum and optionally in the presence of genotoxic, cell cycle (synchronisation) arrest, or stress-inducing agents, and monitoring apoptotic death in said cells. A further assay for determining agents which induce apoptosis in cells, according to the invention comprises administering the agent under test to cells at high cell density in the presence of high serum and at least one of genotoxic, cell cycle arrest, or stress-inducing agents, and monitoring apoptotic death in said cells.

Novel agents identified using these assays form yet a further aspect of the invention, as does the use of known reagents identified using these assays in the induction of apoptosis. These assays have the potential to identify agents which may overcome the cancer cell's resistance to conventional radio or chemotherapeutic agents.

As used herein, the expression "cell cycle arrest agent" refers to agents which induce proliferation arrest at particular stages within the cell cycle. The induction of proliferation arrest within mitosis can be monitored by observation of an increase in the numbers of cells with condensed chromosomes in a mitotic stage-specific, such as metaphase, configuration; proliferation arrest at other cell cycle stages can be assessed for example by a reduction in the incorporation of bromodeoxyuridine or tritiated thymidine into DNA or by a reduction in the expression of proliferation-associated antigenic markers such as proliferating cell nuclear antigen (PCNA) or Ki67. Examples of agents which induce arrest within mitosis include Methyl [5-(2-thienylcarbonyl)-1H-benzimidazol-2-yl]carbamate (known as nocodazole) and taxol (from Taxus brevifolia).

The agents of the invention may be used alone or in combination or complexed with each other or with chemotherapeutic or irradiation agents or with cell cycle arrest (synchronisation) agents. An apoptotic effect is seen on cells in tissue culture when the agents of the invention are employed at doses which are normally sublethal, or under conditions which normally protect against death, in conjunction with sublethal doses of irradiation or chemotherapeutic agents. A similar synergistic effect is expected on tumour cells in vivo which is less likely to be dependent on the tumour environment than if the agents of the invention are administered alone. This approach also has the potential of achieving a therapeutic effect with less toxicity to the patient.

It appears that delta agonists may have a role in either rescuing or accentuating the apoptotic effect depending upon the dose and mode of application as described hereinafter. Hence they may be suitable agents for combining with the agents of the invention.

The dosage of the various agents which is required in order to generate the desired effect will depend upon the particular agent used, the nature of the condition and the precise nature of the effect required. The appropriate dosage in any particular case will be determined by the physician.

Agents as described above, when used in therapy, for example in the treatment of malignant tumours, are suitably applied in the form of a composition in combination with a pharmaceutically acceptable carrier or excipient. Examples of such carriers include both liquid and solid carriers such water and saline.

Various methods of administration of the therapeutic agent can be used, following known formulations and procedures. The administration may be systemic or targeted, the latter employing direct (eg topical) application of the the therapeutic agent to the target cells or the use of targeting systems such as antibody or cell specific ligands. Targeting may be desirable for a variety of reasons; for example if the agent is unacceptably toxic, or if it would otherwise require too high a dosage, or if it would not otherwise be able to enter the target cells.

Instead of administering these agents directly, they could be produced in the target cells by expression from an encoding gene introduced into the cells, eg in a viral vector (a variant of the VDEPT technique—see below). The vector could be targeted to the specific cells to be treated, or it could contain regulatory elements which are switched on more or less selectively by the target cells.

Alternatively, the agent could be administerd in a precursor form, for conversion to the active form by an activating agent produced in, or targeted to, the cells to be treated. This type of approach is sometimes known as ADEPT or VDEPT; the former involving targeting the activating agent to the cells by conjugation to a cell-specific antibody, while the latter involves producing the activating agent, eg an enzyme, in a vector by expression from encoding DNA in a viral vector (see for example, EP-A-415731 and WO 90/07936).

As mentioned briefly above, the invention also relates to the induction of apoptosis in the lens cells of the eye and the application of this in cataract surgery.

In individuals undergoing surgery to remove cataractous eye lens a major complication is the regrowth and differentiation of cells on the posterior and anterior faces of the replacement intraocular lens.

Cataract is a major cause of blindness throughout the world with the highest incidence in the Third World. In addition the incidence of cataract is greater in old age increasing from 5% (52–64 years) to 18% (65–74 years) and up to 46% (75–80 years, Kahn et al., 1977, Am. J. Epidermiology, 106, 17–27). Operations to remove cataracts are the main reason for ophthalmological hospital admission and the sixth commonest large operation overall (Bloemendal et al., in Biochemie des Anges (Hockwin O., ed), Erike Verlag, Stuttgart (1985, 82–109). Cataract surgery involves either complete removal of the lens or more commonly opening of the lens capsule and removal of the lens contents. This includes most of the fibre cells (which make up the bulk of the lens) and the majority of the anterior epithelial cells. This leaves the lens capsule as an empty sack into which can be placed an artificial lens (or intraocular lens) to correct the patient's vision. The implant can be located within the capsule or supported on the iris with loops holding the implant into the capsular bag.

The most common complication following extracapsular extraction (ie. where the lens content is removed leaving behind the capsule sack), regardless of whether an intraocular lens is fitted, is opacification of the implant. This results from the growth of cells or the presence of other debris on the anterior surface of the implant. More commonly, however, opacification results from the growth of cells on the posterior capsule: known as after cataract. This regrowth is less common (9–18% of cases) where the implant is placed within the capsule compared to all extracapsular operations (40–50%). After cataract is believed to result from the outgrowth of residual epithelial cells from the periphery of the lens onto the posterior capsule. These cells cause capsule wrinkling and may also differentiate into fibre cells resulting in the formation of cell clumps called Elschnig's pearls (Sveinsson, 1993, Acta Ophthamologica, 71, 95–98). In either case the result is pacification of the implant with loss of clear vision for the patient. This can be corrected by a second implant or by laser treatment, the latter commonly resulting in further complications.

Epithelial cells in the normal lens spontaneously undergo programmed cell death or apoptosis during early development (Ishizaki et al., 1993, J. Cell Biol. 121, 899–908), however this is restricted to the central epithelium over the suture lines (point at which mature fibre cells meet). In adult, apoptotic epithelial cells are very infrequent except in patients with cataracts (Li et al.m 1995, J. Cell Biol., 130, 169–181). Indeed it has been suggested that cataract patients may have deficient defence mechanisms against commonly encountered lens insults such as oxidative stress and ultra violet light. These may lead to epithelial cell apoptosis and initiate cataract. It would be advantageous in one could utilise the lens cell's apoptotic tendency to remove contaminating epithelial (and other) cells from the intraocular lens implant and thus prevent opacification.

In a particular embodiment of the invention, agents which will induce apoptosis in mammalian cells are used as a coating or adjunct to the intraocular lens in order to prevent the growth and differentiation of cell on the implant following cataract operations. This treatment will be particularly efficient on intracapsular implants since it will enhance the restriction on cell growth already demonstrated with this type of implant. However, treatment of the anterior face of these and other implants would prevent growth of cells such as fibroblasts on the anterior of the implant. Apoptosis inducing factors on intracapsular implants would not have access to the rest of the eye and so would not effect other ocular tissues such as the retina and the cornea. Indeed treatment could be restricted to those areas of the capsule likely to encounter surviving epithelial cells such as the anterior edges and posterior—both regions covered by the capsule sack.

Agents which may be of use in this form of treatment include:
i) DNA damaging agents such as Etoposide, Staurosporin and Mitomycin C;
ii) agents which cause oxidative stress to cells such as hydrogen peroxide and Diamide;
iii) agents which elevate intracellular calcium such as ionomycin, calcimycin (A23187) and thapsigargin;
iv) growth factors causing cells to undergo apoptosis such as TGFβ;
v) agents which elevate intracellular sugar levels such as galactose and glucose;
vi) agents which act through opiate receptors s and in particular an agent which acts as an antagonist at receptor(s) related or identical to the delta opioid receptor, or an agent which acts as an agonist at receptor(s) related or identical to the kappa opioid receptor such as naltrindole and U50488;
vii) glucocorticoids such as methylprednisolone; and
viii) agents which prevent cell division and progression through the cell cycle such as toxol, cochinine, aphidicolin, nocodazole, vinblastine;
viii) agents which are able to neutralise proenkephalin or its proteolytic derivatives; or
ix) an agent which increases the level of nuclear proenkephalin and/or its derivatives, or which activates or mimics them.

Combinations of these agents may be more effective than when used alone. For example, it has been shown that sub-lethal doses of agents such as Naltrindole and U50488 used in combination will induce lens cell apoptosis. Indeed such combinations will confer selectivity in situations where cells other than lens cells may be encountered, eg. iris-supported implants.

These drugs have been shown to be effective at killing other undifferentiated cells whilst not affecting fully differentiated cells such as are found in the retina for example. Epithelial cells derived from the lens are non-differentiated and will therefore be killed before they have the opportunity to migrate out onto the posterior capsule and undergo differentiation into fibre cells (Elschnig's pearls).

As mentioned above, Raff (1992 Nature 356, 397–400; Raff et al., 1993 Science 262, 695–699) has proposed that all mammalian cells require factors from surrounding cells to prevent their death by apoptosis. Using the lens as a model system he has demonstrated that at least in vitro lens epithelial cells require such factors in order to survive. Indeed since these cells live for the life of the individual they will require a high level of survival factors.

The survival factors can be derived from surrounding cells as autocrine factors or from serum as endocrine or paracrine factors (Ishizaki et al., 1993 J. Cell Biol. 121, 899–908). However despite testing numerous growth factors, some known to act on the lens and some not, he was unable to identify the factor(s) necessary for lens cell survival.

Using antibodies raised against proenkephalin we believe we have identified at least one factor necessary to prevent lens cell apoptosis as will be illustrated in the following examples. Proenkephalin, as judged by immunofluorescence microscopy and immunoblotting, is very abundant in the lens, particularly in the anucleate fibre cells. Thus the apoptosis inducing agents based upon proenkephalin or its derivatives as discussed above may be particularly suitable.

Hence two drugs which we believe interact with the putative proenkephalin receptor (Naltrindole and U50488, have been found to induce apoptosis in lens epithelial cells in culture, though their effect is less marked than for example transformed cell lines. Other agents which induce apoptosis in other cell types, eg. etoposide, staurosporin, mitomycin C, hydrogen peroxide, TGFβ also induce apoptosis in lens epithelial cells in culture. Using time-lapse video microscopy etoposide, staurosporin, mitomycin C, naltrindole and U50488 have been shown to induce apoptosis in a number of cell lines derived from the lens epithelium. These include both cell lines such as a rabbit lens cell line (NN1003A, Reddan et al., 1986) and mouse lens cell line αTN4, Nakamura et al., 1989) and primary lens epithelial cells derived from the bovine lens. Protection from apoptosis induced by these compounds was afforded by incubation of the cells in high serum or at high cell density. Lens cells were more resistant to the compounds than a number of tumour derived cell lines (e.g. HeLa cells), they were however more readily killed by combinations of the apoptosis inducing compounds.

In the following description, reference will be made to the attached Figures in which.

Figure 3:
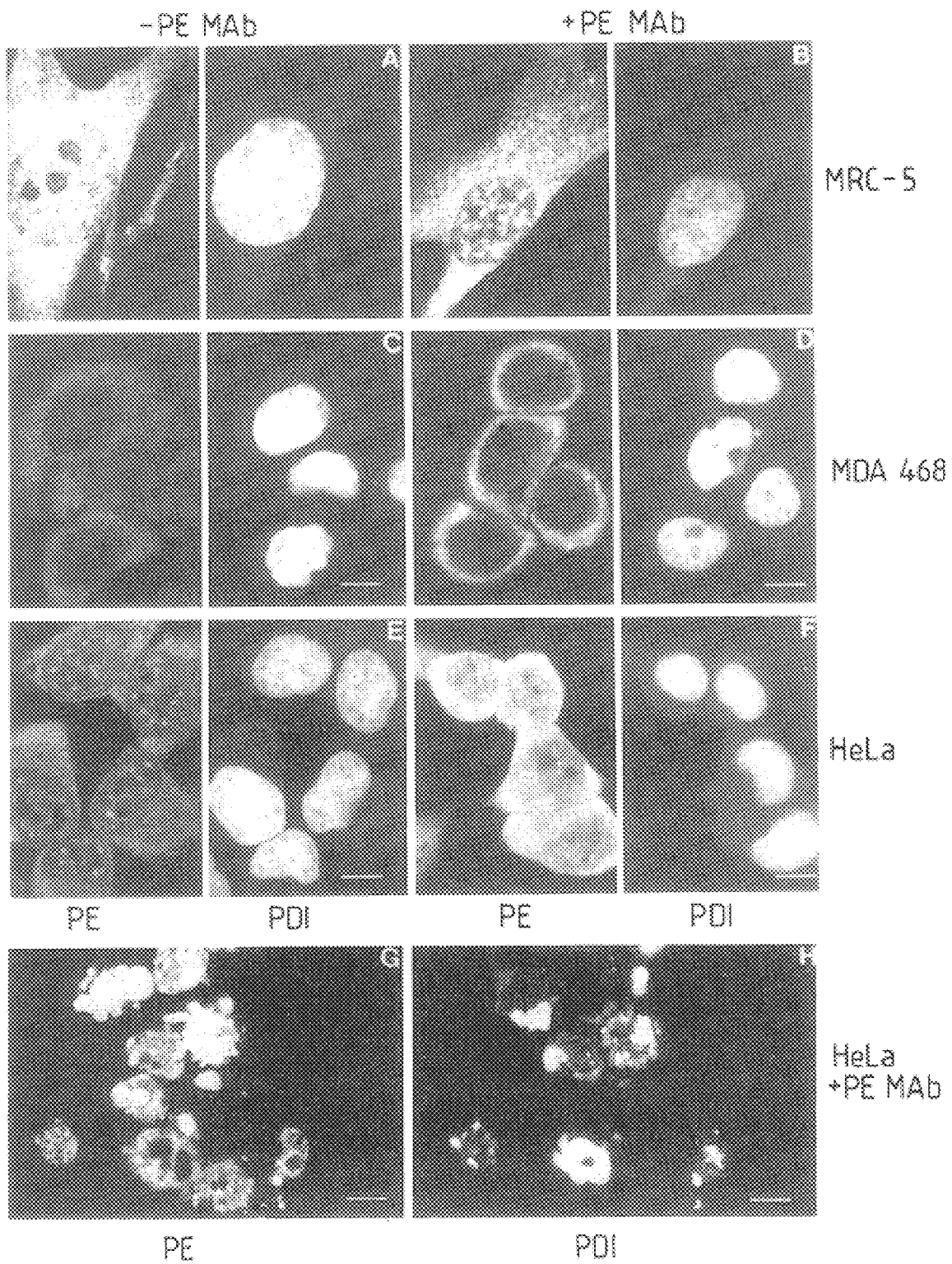

FIG. 3 shows fluorescence micrographs of MRC-5, HeLa, and MDA 468 cells in the presence (right hand panels) and absence (left hand panels) of PEmAb. Cells were stained with the nucleic acid dye propidium iodide (PDI) to reveal nuclear features and with PE mAb after the challenging antibody had been washed off, to reveal endogenous proenkephalin (PE) staining: Panels D, F show sublethally affected cells; panels G, H show overtly apoptotic HeLa cells after mAb treatment;

FIG. 4 shows the partial amino acid sequences encoded by the anti-proenkephalin immunoglobulin heavy chain variable domain genes; and FIGS. 5A and 5B show the amino acid sequence of proenkephalin in which the epitopes recognised by anti-proenkephalin antibodies are shown.

In a series of experiments, based on the use of a series of monoclonal antibodies to recombinant proenkephalin expressed in bacteria, the following was noted:

1) Upregulation of cytoplasmic proenkephalin in serum deprived 3T3 and 3T3 cells maintained at high density.

It has been found that cytoplasmic proenkephalin is upregulated in 3T3 cells when deprived of exogenous survival factors, which suggests that endogenous proenkephalin may compensate for a reduction in exogenous survival factor signalling. It was further found that whilst proenkephalin exists predominantly as a nuclear protein in proliferating non-transformed Swiss 3T3 cells (Bottger and Spruce, J. Cell Biol. 1995 in press), it undergoes cytoplasmic upregulation if cells are grown to and maintained at high density. Published data indicate that cells at high density resist apoptosis for a number of reasons. The inventors found that high density 3T3 cells resist oxidant damage-induced apoptosis substantially better than low density 3T3 cells, the protection being derived predominantly from non-diffusible signals. Taking the data together, it was thought that high density cells are protected from oxidant damage due to upregulation or activation of proenkephalin on a pathway activated at high cell density by nondiffusible factors. Tests were then carried out to see whether proenkephalin promoted survival by overexpression of the gene in cell lines (see exemplification hereinafter).

2) Existence of proenkephalin in astrocytes.

The applicant has shown by immunofluorescence that proenkephalin exists in vivo and in vitro in the cytoplasm of (serum maintained) astrocytes (Spruce et al., 1990 EMBO J. as above). Other laboratories have confirmed that unprocessed proenkephalin is released from astrocytes, together with processing enzymes which may then permit extracellular cleavage to enkephalin peptides (see introduction). Astrocytes are cells which are primed to proliferate throughout life, in response to neural damage or disease. The applicant has reasoned that these cells may need to be released from the coupling between the receipt of signals from exogenous survival factors and the decision whether to die or proliferate. This would permit a proliferative response to neural damage even when exogenous survival factors were limiting. It would be predicted that this might be associated with a greater propensity for malignant transformation, which appears to be the case since astrocytes are the commonest cell type to give rise to brain tumours. The existence of proenkephalin in astrocytes may confer an autonomous survival advantage which allows these cells to override the normal apoptotic safeguard against proliferation independent of the growth environment.

3) Existence of proenkephalin in the lens of the eye.

As described earlier, Raff has proposed that lens cells are dependent for their survival on autocrine factors which have yet to be identified. Immunofluorescence and immunoblotting, using anti-proenkephalin antibodies, showed that proenkephalin and/or proenkephalin-derived peptides exist at apparently high levels in the lens of the eye. This would indicate that proenkephalin and/or its products are acting as autocrine survival factors to protect lens cells which are devoid of a supply of exogenous survival factors. A proportion of proenkephalin and/or its high molecular weight cleavage products appears, by immunofluorescence, to be bound to cell surface membranes in the interior of the lens. Immunoblot analysis of membrane fractions from the lens supports the possibility that a proportion of proenkephalin is membrane-bound. It is therefore likely that proenkephalin and/or its high molecular weight cleavage products are binding to cell surface receptors after release. Alternatively, since there is little extracellular space in the lens, proenkephalin may not be released but may remain bound to the membrane and exert an extracellular survival effect through extracellular revelation of functional domains. In addition, immunoblot analysis of membrane fractions using anti-proenkephalin antibodies appears to show the existence of several high molecular weight cleavage products of proenkephalin. This raises the possibility that cleavage of proenkephalin may occur through the action of membrane-bound endoproteases.

4) Proenkephalin becomes decoupled from density-dependent signalling during spontaneous transformation of 3T3 cells.

In proliferating non-transformed 3T3 cells proenkephalin exists predominantly as a nuclear protein (Bottger and Spruce 1995 J. Cell Biol, 130, 1251–1262). If 3T3 cells are grown to high density cytoplasmic proenkephalin becomes unmasked which reflects its activation. If 3T3 cells are maintained at high density in low serum, spontaneous transformation is encouraged. At the point when cells acquire anchorage-independence cytoplasmic proenkephalin immunostaining becomes further upregulated. In cells which have progressed to an overtly transformed state cytoplasmic proenkephalin remains unmasked in cells grown at low density. Therefore, proenkephalin has become decoupled from density-dependent signalling during spontaneous transformation.

Normally, when cells outstrip their supply of exogenous survival signals cell suicide is induced. It was thought that the acquisition of a proenkephalin-dependent survival advantage may provide a cell with an increased capacity to survive when the cell becomes anchorage-independent and thereby receives reduced cell-cell contact or cell-matrix survival signals or a lesser amount of short-range soluble survival signals. The prediction is that this would contribute to tumour progression.

5) Cytoplasmic upregulation of proenkephalin in apoptotic cells in vivo and in vitro.

In in vivo models of apoptosis (androgen-deprived rodent prostate and corticosteroid treated thymus), proenkephalin is upregulated in cells with typical features of apoptosis. This was found using anti-proenkephalin antibodies in immuno-histochemal analysis of tissue sections. The upregulation was confirmed by the applicant in cells in tissue culture induced to become apoptotic with DNA damaging drugs, UV irradiation, or by induction of a transfected c-myc gene. The upregulation of proenkephalin in established apoptotic cells is believed to reflect either a final cell autonomous rescue attempt, or an attempt by the apoptotic cell to promote the survival of surrounding sublethally damaged cells which might promote overall tissue recovery.

6) Upregulation of proenkephalin in mitotic and meiotic cells.

A marked diffuse upregulation in proenkephalin immunostaining in mitotic cells at all stages of mitosis has been observed. The staining is excluded from condensed chromosomes and often has a secretory vesicle-like quality in addition (unpublished data). The applicant has reasoned that the upregulation of proenkephalin in mitotic cells may reflect the upregulation of a survival factor at a vulnerable stage of the cell cycle when mitotic kinases, which may have a dual role in the apoptotic process, are activated. The applicant and co-workers have also noted upregulated proenkephalin in the nucleus and cytoplasm of meiotic (spermatogenic) cells.

7) Cytoplasmic upregulation of proenkephalin in cells that have received a sublethal dose of DNA damaging drugs or ultraviolet (UV) irradiation.

Following the discovery that proenkephalin is upregulated in apoptotic cells, investigations were made to determine whether this upregulation might be secondary to apoptosis-induced DNA damage and/or stress. Fibroblasts (3T3 cells, grown in Dulbecco's modified Eagle's medium, DMEM, containing 10% fetal calf serum) treated with UV irradiation or the DNA damaging agents etoposide and mitomycin, show early, synchronous changes in the subnuclear organisation of proenkephalin which precede the onset of apoptosis; since the onset of apoptosis is asynchronous a correlation between the two could not be drawn.

The most striking observation from this series of experiments was a very marked, transient cytoplasmic upregulation (sometimes accompanied by nuclear upregulation also) of proenkephalin in cells that had received a sublethal insult. This response occurs earlier with lower doses of UV irradiation or at higher cell density. Specifically, cells grown at low density treated with a UV dose of 50 Joules m-2 show this response as late as 7 days; cells grown at higher density show this response much earlier at around 1 day. Cells at high density treated with a lower dose of UV (25 Joules m-2) show cytoplasmic upregulation at around 12 hours. This may reflect a "survival response" in cells that had received a sublethal insult. Cells may be rescued more promptly at higher density due to the effect of secreted or non-diffusable survival factors, which are not necessarily opioid-like factors, which signal an intracellular survival response.

Confluent (dense) Swiss 3T3 cells were also exposed to the drug etoposide, which induces DNA damage, at a concentration of 50 $\mu$M. Under these conditions, there is no evidence of apoptosis but there is an early (at around 8 hours), marked cytoplasmic and nuclear upregulation of proenkephalin. In contrast, when the DNA damaging drug mitomycin is administered to confluent 3T3 cells at a dose of 10 $\mu$g per ml, the majority of cells undergo apoptosis within 40 hours. There is a very late, moderate upregulation of proenkephalin in established apoptotic cells (consistent with upregulation of proenkephalin in other apoptotic systems) but there is no upregulation in non-apoptotic cells. The applicant reasons that this reflects a failure to mount a successful rescue attempt in the face of a catastrophic insult.

A prominent feature of the cytoplasmic upregulation of proenkephalin in sublethally damaged cells is its apparent co-distribution with the endoplasmic reticulum, confirmed by co-immunostaining with an antibody to the "KDEL" motif which is a marker for this subcellular compartment. A similar distribution was noted in cells which had received hydrogen peroxide or a heat shock. This subcellular distribution is similar to that of the bcl-2 intracellular survival molecule (Jacobson et al., 1993 Nature 361, 365–369), and raises the possibility that intracellular proenkephalin may be interacting with this protein. The upregulation of proenkephalin in this distribution occurs earlier the higher the cell density which suggests that autocrine survival factors may be inducing the upregulation of intracellular proenkephalin, which can be compared with the known upregulation of intracellular bcl-2 by exogenous survival signals. Subsequent analysis of sublethally damaged cells indicated that proenkephalin is also located in a secretory-vesicle-like distribution suggesting that proenkephalin is also itself an extracellular or cell surface membrane bound survival factor.

These observations led to the formulation of the present invention, evidence for which can be summarised as follows:
1. Proenkephalin participates in a pathway which mediates cell density-dependent repression of apoptosis.

Non-transformed 3T3 cells at high density resist oxidant damage substantially better than cells at low density. Conditioned medium from high density cells fails to transfer protection to low density cells. Therefore protection from oxidant damage at high cell density derives predominantly from nondiffusible factors, although additional protection from ultra-labile short-range soluble factors cannot be excluded. Cytoplasmic proenkephalin is revealed, which is likely to reflect its activation, when 3T3 cells are grown to high density. Proenkephalin immunostaining is transiently upregulated to a greater degree when cells are subjected to sublethal oxidative or genotoxic injury, a response with is accelerated at high cell density and is predictive of survival outcome. Collectively, these data indicate that proenkephalin dependent repression of apoptosis is at least partly mediated through a pathway activated at high cell density or nondiffusible factors. The prediction is that inappropriate activation of such a pathway would decouple a cell from its environment and therefore contribute to tumorigenesis.

2. Overexpressed cytoplasmic proenkephalin is a repressor of apoptosis close to the final pathway(s) which execute the death programme.

To test directly whether proenkephalin protects cells from apoptosis, cell lines of more than one type in which proenkephalin is overexpressed following stable gene transfer were studied. In these lines overexpressed proenkephalin confers protection from apoptosis induced by oxidants for example hydrogen peroxide and also the kinase inhibitor staurosporine. In these cells the transfected gene product accumulates at the site of the endoplasmic reticulum but a proportion also progresses to the secretory pathway. The repression of apoptosis in transfected compared to control cell populations was confirmed using a number of parameters. In proenkephalin-overexpressing cells the protection from apoptosis is sustained.

The sustained protection from staurosporine-induced apoptosis indicates that proenkephalin is a general repressor of apoptosis and that is acting close to the final pathway which executes the death programme rather than at an upstream precommitment point. A wide range of cell types is susceptible to staurosporine-induced apoptosis which is not inhibited by inhibitors of new protein synthesis. Therefore, staurosporine is acting on molecules which interact with or comprise the machinery which executes the intrinsic death programme and which is constitutively in place in most if not all cells.

The protection conferred by proenkephalin from genotoxin- and oxidant-induced apoptosis indicates that proenkephalin may prevent cell suicide in response to genetic damage sustained as a result of environmental insults; this would implicate a proenkephalin-dependant pathway in early stages of oncogenesis.

All cells appear to possess an intrinsic death programme which runs by default if cells are deprived of extracellular survival signals. To test whether proenkephalin may help a cell to override its need for extracellular survival signals, cells in which cytoplasmic proenkephalin was stably overexpressed were cultured at low density in the absence of soluble survival factors. Unlike many cell types, proenkephalin-overexpressing cells could support their own survival under these conditions. The applicant went on to test whether proenkephalin-overexpressing cells could survive the complete deprivation of exogenous signalling molecules by isolation as single cells. It was found that some proenkephalin-overexpressing cells survive for extended periods. These results indicate that excessive activation of a proenkephalin-dependent pathway will help a cell overcome its need for exogenous survival signalling and will therefore contribute to tumour progression and metastatic spread. This result therefore confirms the prediction that proenkephalin contributes to tumour progression from the data which showed that proenkephalin becomes decoupled from density-dependent signalling during spontaneous transformation of 3T3 cells.

Thus, dysregulation of a proenkephalin-dependent pathway which represses apoptosis is implicated at early and later stages of oncogenesis.

3. In transformed cells proenkephalin and/or its products act as extracellular or cell surface membrane-bound factors which modulate the balance between survival and death.

Extracellular administration of purified anti-proenkephalin monoclonal antibodies induces apoptosis in cultured tumour cells including cervical carcinoma (HeLa) and breast carcinoma (MDA 468); however, non-transformed cells such as MRC-5 cells are unaffected (FIG. 3). If cells are analysed at a single time point, there is at maximum a 7-fold increase in the number of apoptotic cells; however, since apoptosis is a short-lived process, the overall rate of apoptotic induction is likely to be significant. Also, even cells which are not overtly apoptotic show some shrinkage and modest chromatin condensation as shown, features which are not seen in anti-body-treated MRC-5 cells. Furthermore, since the anti-proenkephalin antibodies appear to interfere with mitotic progression, apoptosis will be unopposed by cell production. The apoptotic effect is greatest when cells are deprived of exogenous survival factors (challenged with antibody in the presence of a low concentration of fetal calf serum) and are at low density.

These findings indicate that tumour cells are more dependent than non-transformed cells on released or cell surface membrane bound proenkephalin and/or its proteolytic products for survival. The applicant has reasoned that activation of a proenkephalin-dependent survival pathway, perhaps through a genetic event, during the transformation process may have downregulated alternative survival pathways or molecules in an attempt to compensate for the cell's perception of an inappropriate survival signal. A remaining possibility is that extracellular or cell surface membrane bound proenkephalin has an opposite effect to cytoplasmic proenkephalin and mediates death rather than survival; antibody-mediated cross-linking of proenkephalin bound to a cell surface receptor may therefore activate a pathway which mediates death.

4. Tumour cells show enhanced dependence on signalling at delta opioid-like receptors for survival when exogenous survival signals are diminished or when the cell as suffered a genotoxic insult, oxidative or some other stress.

Extracellular administration of a synthetic antagonist which binds preferentially to the delta opioid receptor, naltrindole, induces apoptosis in up to 100% of tumour cells cultured in low serum at low density within 1 hour. Apoptosis proceeds at a slower rate in high serum at high density. The effect is enhanced in low serum and at low cell density. The dose of drug required to achieve an effect is substantially higher than the reported inhibition constant of the drug for the cloned delta receptor. Possible reasons for this are that the opioid receptor to which this compound is binding is not the delta receptor itself but is related to it or is a non-reported subtype; the delta receptor is mutated in tumour cells, thereby changing the affinity of the receptor for the compound; there is heterooligomeric complexing of the delta receptor with another receptor which could also change its affinity for the compound; there is coupling of the delta receptor with another receptor acting in opposition to it in which case the kinetics of the binding of the antagonist may be important so there is insufficient time for a compensatory rescue.

If cells are treated with the delta receptor agonists "DPDPE" and "DSLET" together with naltrindole, either protection from or accentuation of apoptosis is seen. Accentuation or protection appears to depend on dose and timing of the administration of the delta agonists. Accentuation of an apoptotic effect would be consistent with a paradoxical antagonist effect of delta receptor agonists due to receptor internalisation, described in other systems. No effect is observed either with delta agonists on their own or with the mu receptor agonist "DAMGO" alone or in combination with naltrindole.

There is little if any apoptotic effect (transient "zeiotic-type" blebbing only) with the less selective opioid receptor antagonists naloxone and naltrexone. These agents have a lower affinity for the delta compared with mu and kappa receptors. Antagonism at delta or delta-like receptors may also be counteracted by antagonism at kappa or kappa-like receptors (see later).

Cells subjected to genotoxic injury and/or stress, for example with ultraviolet irradiation or with the drug etoposide, show a greater degree of DNA damage if these treatments are co-administered with naltrindole, even in the presence of high serum. This indicates that naltrindole can sensitise cells to genotoxic agents.

Therefore, antagonism of the delta or a related opioid receptor induces apoptosis which can be partially prevented with agonists for the delta or a related receptor, or other times is accentuated. The conditions required for enhanced (maximal) activity of the drug naltrindole indicate that the delta opioid, or a related, receptor, promote cell survival in the face of genotoxic injury or when cells are in an environment with suboptimal amounts of exogenous survival factors.

5. Opiate-like molecules promote apoptotic death to redress the potential for opiate-like molecules to confer an autonomous survival advantage.

Extracellular administration of a synthetic agonist for the kappa opioid receptor, U50488, induces apoptotic death in up to 100% of tumour cells within 1 hour. Again, there is an enhanced (maximal) effect in low serum and at low cell density which suggests coupling of a kappa-like receptor mediated death response to a delta receptor-likemediated survival response. More direct evidence for this is provided by evidence of synergism between naltrindole and U50488 which have a greater than additive effect when co-administered.

High (10%) fetal calf serum affords a greater degree of protection against kappa agonist induced death than delta antagonist induced death. This indicates exogenous survival factors in serum may downregulate a kappa-like receptor-mediated death pathway, but that this rescue requires continued signalling through a delta-like survival receptor to be maximally effective.

Co-administration of U50488 together with the DNA damaging drug etoposide induces apoptotic death at doses of each drug which are sublethal when administered individually. Although high serum protects cells to a greater extent from the effects of the drug U50488 than the drug naltrindole when administered alone, the combination of U50488 and etoposide in high serum is very effective in inducing apoptotic death. Therefore, combining the drug U50488 with a DNA damaging drug such as etoposide, has the potential to give a therapeutic effect which is independent of the "survival environment" of the tumour.

Another approach to combination therapy, using agents which induce cell cycle arrest (cell cycle synchronisation techniques), is indicated by the effect of pre-treatment with the drug nocodazole, which induces cell cycle arrest within mitosis at metaphase, followed by U50488. A marked apoptotic effect is seen, even when cells are at high density, when these two agents are given in this way.

Together, these data indicate that a kappa-like opioid receptor mediates death and that this pathway is coupled to a delta-like opioid receptor-mediated survival pathway. Agonist activation of a kappa-like receptor death pathway is enhanced in the face of exogenous survival factor deprivation, genotoxic damage, or cell cycle arrest (synchronisation). This may reflect a compensatory upregulation of a death pathway in response to activation of a (delta-like opioid receptor) survival pathway which confers a potentially dangerous autonomous survival advantage to a cell.

6. Tumour cells are more sensitive to anti-proenkephalin antibodies and to opiate-like receptor ligands.

Anti-proenkephalin antibodies, naltrindole, and U50488, all have a greater apoptotic effect on tumour compared with non-transformed cells. Anti-proenkephalin antibodies have no effect on (non-immortal) MRC-5 cells (human embryonic fibroblasts) and only have an effect on immortalised (non-transformed) fibroblasts such as 3T3 and Rat-1 cells if these have been subjected to a prior period of serum deprivation.

Naltrindole and U50488 induce apoptosis in cultures of all cancer cell lines so far tested including HeLa (cervical carcinoma), MDA 468 (breast carcinoma), A431 (vulval carcinoma), Hep-2 (head and neck squamous carcinoma), and all of the following ovarian carcinoma lines—CH1, PXN94, SKOV-3, A2780. There are, however, differing sensitivities and some have a preferential response for one of the compounds. In contrast, both drugs have a lesser effect on non-transformed cells such as primary cultures of cells isolated from the lens of the eye. Furthermore, whereas proliferating, undifferentiated muscle cells in tissue culture are sensitive to both drugs, these cells become resistant to both drugs after differentiation.

7. Overexpression of proenkephalin targeted to the nucleus induces apoptotic death in some cell types.

Transfected proenkephalin can be targeted to the nucleus if it is mutated to remove the signal peptide sequence (PEΔSS) or if the normal ATG translation initiation codon is mutated (PE ATC) so that translation is forced from a codon downstream (Bottger and Spruce 1995, J. Cell Biol. In Press). COS cells but not 3T3 cells tolerate nuclear overexpression of proenkephalin. It was felt that this may be due to the overexpression of SV40 large T antigen in COS cells in which p53 function is therefore inactivated. To test whether the induction of death by nuclear proenkephalin may require p53 function, C6 rodent fibroblasts which harbour a temperature sensitive mutant form of p53 were transiently transfected with proenkephalin cDNAs encoding products which would be targeted exclusively to the cytoplasm (PE+SS) or the nucleus as well (PEΔSS and PE ATC). At 37° C. when p53 is in its mutant and therefore inactive conformation, transfected cells appear somewhat shrunken but are viable; in contrast, at 32° C. when p53 is in its wild-type conformation very few transfected cells are seen and those that are have an apoptotic appearance. Stable C6/ts p53 lines have also been generated which overexpress nuclear proenkephalin, in some of which apoptotic cells are present even at 37° C. but these are increased at 32° C.; this may reflect the retention of some wild-type p53 function at 37° C. Cells which are not overtly apoptopic at 37° C. show evidence of DNA damage such as micronuclei. These experiments indicate that overexpressed nuclear proenkephalin induces DNA damage dependent apoptosis which is at least partly p53 dependent. Tumours which retain normal p53 function are therefore a particular target for pro-apoptotic agents which simulate overexpression of transfected proenkephalin targeted to the nucleus.

The following examples illustrate the invention.

Example 1

Overexpressed cytoplasmic proenkephalin represses apoptosis induced by oxidant damage and staurosporine, and by deprivation of exogenous survival signals.

Experiments in which 3T3 cells were subjected to sublethal oxidative or genotoxic injury indicated that proenkephalin mediates the repression of apoptosis at least partly on a pathway activated at high cell density. In order to test directly whether proenkephalin promotes cell survival, stable lines which had been transfected proenkephalin cDNA were examined. In these lines transfected proenkephalin is localised exclusively in the cytoplasm. Since 3T3 cells are relatively resistant to stable transfection procedures, other cell types were chosen.

Figure 1:
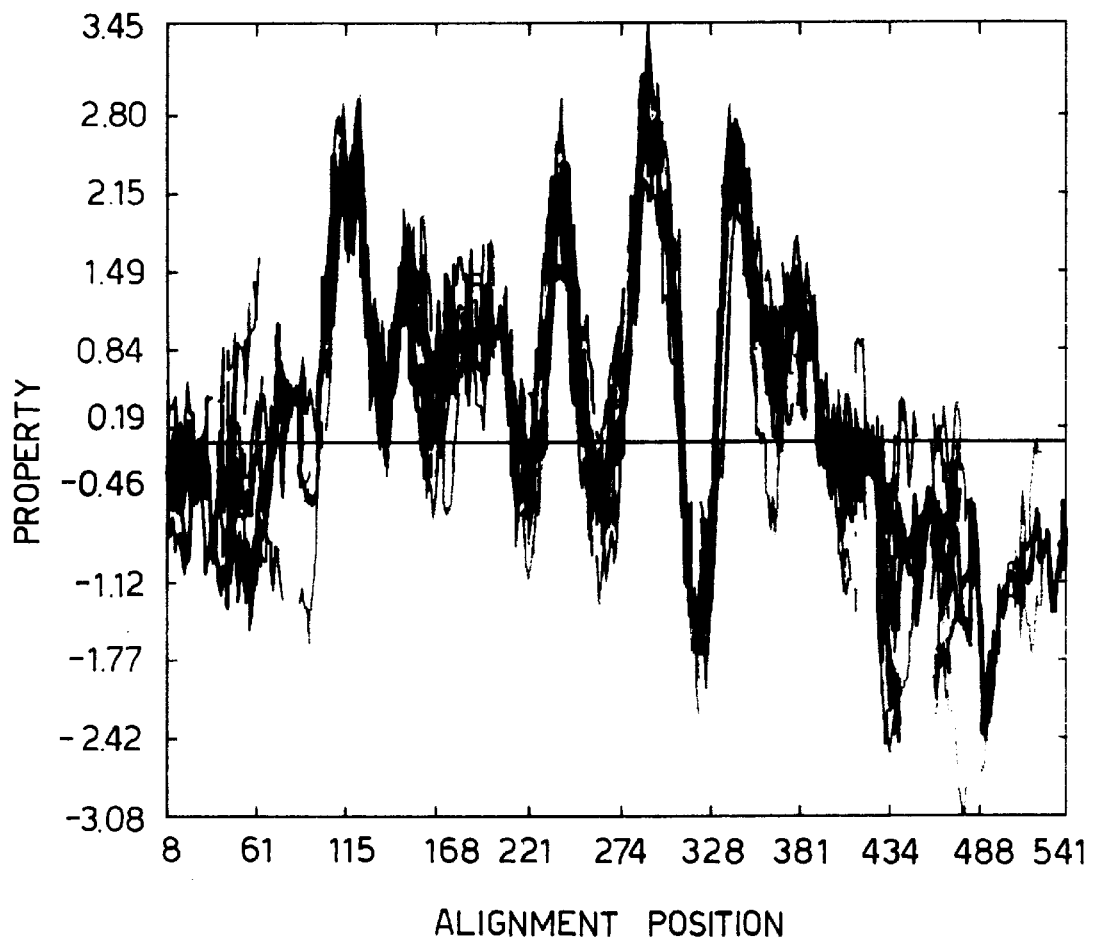
FIG. 1 is a computer-generated comparison of hydropathy plots for aligned opiod and somatostatin receptors.
Figure 2:
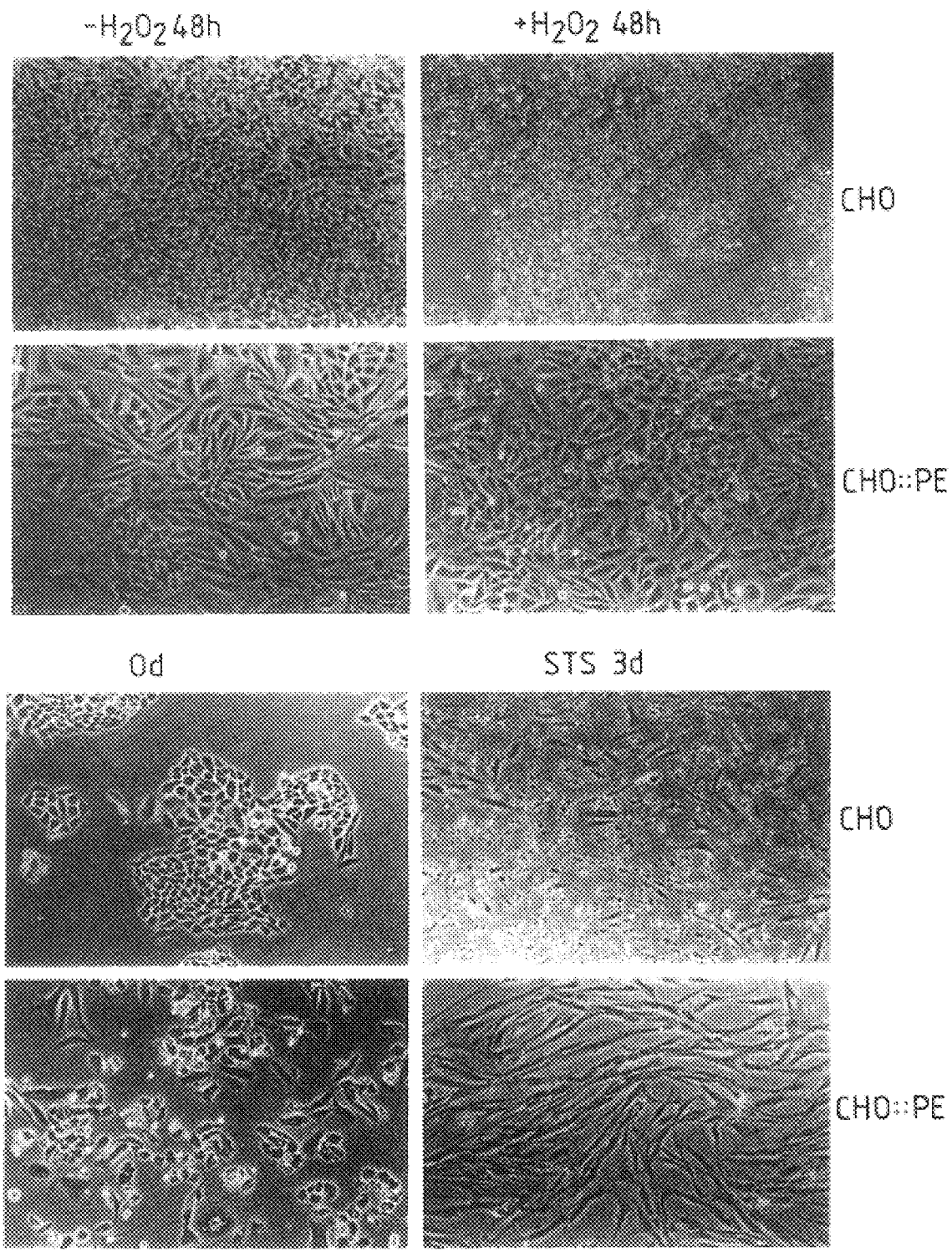
FIG. 2 shows phase contrast micrographs comparing hydrogen peroxide and staurosporine treated CHO and CHO::PE cells.

Chinese hamster ovary cells which overexpress proenkephalin (CHO::PE) at a high level by co-amplification with the dihydrofolate reductase gene through step-wise increases in methotrexate were compared with non-transfected CHO cells for their ability to resist apoptosis induced by agents including hydrogen peroxide and staurosporine. Cells were treated with 2 mM hydrogen peroxide and cell survival assessed over a time course. A number of parameters were used including bulk cell photometric assay of the conversion of the tetrazolium dye MTT as a marker of dehydrogenase activity, which reflects cell viability; numerical scores of apoptopic cells stained with the nucleic acid dye propidium iodide to reveal nuclear features of apoptosis; phase contrast microscopy and time lapse video microscopy. In CHO::PE cells there is an initial decline in MTT conversion over a 24 hour period, but this is substantially less than in CHO cells where MTT conversion becomes unrecoverable, CHO::PE cells go on to survive whereas the entire population of CHO cells eventually die. FIG. 2 (upper panels) shows phase contrast micrographs of CHO and CHO::PE in the presence or absence of hydrogen peroxide ($H_2O_2$) for 48 hours at which time the majority of CHO cells are dead whereas CHO::PE cells are viable and their viability is sustained through to at least seven days.

The ability of CHO::PE cells to resist another inducer of apoptosis, staurosporine, was also tested. Staurosporine is a protein kinase inhibitor which induces apoptosis independently of new protein synthesis; it is therefore acting close to the final pathway(s) which executes the death programme which molecules are constitutively in place in most if not all cells. Exposure of CHO and CHO::PE cells to 5 $\mu$M staurosporine for several days induced death in the entire population of CHO cells whereas CHO::PE cells survived and extended cellular processes, a recognised effect of staurosporine. FIG. 2 lower panels show CHO and CHO::PE cells before and after 3 days staurosporine (STS) treatment.

These experiments indicate that overexpression of proenkephalin in the cytoplasm represses apoptosis close to a focal point common to all death pathways and is therefore likely to be effective in conferring resistance to a wide range of apoptosis inducers. To test whether proenkephalin would protect cells deprived of exogenous survival signals, CHO::PE cells were grown at low density in low serum conditions and were found to survive. To test whether CHO::PE cells would tolerate the complete deprivation of exogenous survival signals, cells were isolated as single cells in Terasaki microwells in the absence of signalling molecules. Raff and colleagues have shown that the majority of normal cell types die within a day if isolated as single cells in this way. It was found that whilst the majority of proenkephalin-overexpressing cells die within one to two days, a minority survive for extended periods for up to six days. The conclusion from these experiments is that proenkephalin overexpression is in itself insufficient to completely override the death programme but that survival is nonetheless improved in the face of deprivation of exogenous signalling molecules. The extended survival in some single cells may reflect either an additional event which has contributed to suppression of the death programme, or suppression of death mediated through proenkephalin which has not yet been opposed by a compensatory activation of a coupled death pathway. Even if dysregulation in a proenkephalin-dependent pathway does not confer survival autonomy at the single cell level, improved survival would still confer a competitive advantage of a cell over its neighbours when faced with a reduction in exogenous signals.

These experiments therefore support the prediction that proenkephalin contributes to oncogenesis at early and late stages.

In case the protection in CHO::PE cells may have reflected a coincident but non-related genetic event, another cell system was examined in which proenkephalin was stably overexpressed, again in a cytoplasmic distribution, in a rodent glioma (C6) cell line under the control of the inducible metallothionein promoter (C6::PE). Control cells which had been through the same procedures of electroporation and drug selection, but which did not express transfected proenkephalin (C6neo), were used as comparators, in case these procedures may have non-specifically selected a more robust population of cells. C6::PE cells are substantially more resistant to oxidant-induced apoptosis than C6neo cells and the protection is increased in the presence of the inducing agent cadmium. Therefore, stable overexpression of cytoplasmic proenkephalin does confer specific protection from apoptosis in different cell types.

Example 2
Extracellular administration of anti-proenkephalin monoclonal antibodies induces apoptosis in tumour cells During spontaneous transformation of 3T3 cells, proenkephalin becomes decoupled from density-dependent signalling and adopts a secretory pathway distribution indicating its release and/or its presentation on the cell surface. The applicant has shown previously that proenkephalin remains at least partially membrane bound within secretory vesicles (Spruce et al., 1988, as above) so that it may become externalised on the cell surface, but not necessarily released, upon exocytosis. Furthermore, evidence from the lens of the eye indicates that proenkephalin and/or its products is cell surface membrane bound.

To determine the effect of neutralising proenkephalin outside the cell or on the cell membrane surface, purified anti-proenkephalin monoclonal antibodies (PE mAbs) were administered to spontaneously transformed 3T3 cells and no effect was observed. However, carcinoma cell lines including HeLa (cervical cancer) and MDA 468 (breast cancer) show an increase in apoptopic cell numbers when treated with PE mAbs. Using FPLC purified antibody, bioactivity was coincident with the immunoglobulim peak. Enhanced apoptopic induction occurs in low serum and at a low cell density. There appears to be little or no effect of PE mAbs on non-transformed cells such as finite life span human fibroblasts (MRC-5 cells).

Antibody concentrations in the region of 6 to 9 $\mu$g/ml typically induced a three-fold increase in the number of apoptotic HeLa cells (from a basal level of around 2% apoptoses rising to 6% after antibody treatment). The maximal effect observed is a seven-fold increase in apoptotic cell numbers. Although these are modest increases, since apoptosis is a very shor-lived process, the overall increase in the rate of apoptosis over a particular time period will be substantially greater.

Apoptotic cells were often observed in clusters. FIG. 3 (panels G and H) shows a typical cluster of apoptotic HeLa cells challenged with purified anti-proenkephalin antibody in low serum. The panel H (propidium iodide, PI, staining) shows grossly fragmented, distorted and pyknotic nuclei. The panel G shows cells stained with anti-proenkephalin antibody (after the challenging antibody had been washed off).

These experiments show that proenkephalin is substantially upregulated in the apoptotic cells, and is in general excluded from the condensed chromatin. Proenkephalin staining also reveals marked zeiotic blebbing. Even in non-apoptotic cells after challenge with anti-proenkephalin antibody, there is upregulation of intracellular proenkephalin (see FIG. 3, (panels D and F) which probably reflects a "rescue" response on the part of the cell.

Since a biological effect was seen with the antibodies PE-13 and PE-15, which are directed to different epitopes on the proenkephalin molecule, it is probable that the effect is due to an inhibition of proenkephalin and not due to antibody binding to a cross-reactive protein. This also suggests that the biological effect is due to immunodepletion of proenkephalin and not due to masking of a receptor binding site on proenkephalin.

The epitopes recognised by the anti-proenkephalin antibodies were mapped using a phage library incorporating randomly generated sequences, illustrated in FIG. 4. The variable domains of the heavy chain anti-proenkephalin immunoglobulin genes were cloned and the amino acid sequences encoded by the heavy chain variable domain genes from fifteen anti-proenkephalin hybridoma lines are shown in FIG. 5.

Antibodies which recognise any of the anti-proenkephalin epitopes, or include the variable domains set out in FIG. 5, form part of the invention.

Further confirmation that antibodies purified by ion exchange FPLC were having a genuine biological effect was obtained, in that a 2 to 3 fold increase in mitotic as well as apoptotic cells was often observed. The observations indicated that there is entry into mitosis but that there may be a failure to complete division since the increase in mitoses is made up almost exclusively of an increase in prophase and metaphase cells. All the prophase and metaphase cells had increased levels of cyclin B1 staining which indicates that these were authentic entries into mitosis.

Additional evidence which suggested a failure of mitotic progression was an increase in the numbers of cells which appear to exhibit simultaneously features of both apoptosis and mitosis which suggests that some cells were aborting their mitosis by entering the apoptotic pathway. However, there were also many cells which had apoptotic features in the absence of mitotic features which suggests that entry into apoptosis was occurring at other cell cycle stages as well.

The observed apoptotic effect of anti-proenkephalin antibodies administered extracellularly is consistent with the action of proenkephalin, or its high molecular weight cleavage products, as extracellular or cell surface survival factors. The greater dependence of established tumour cells compared to newly established transformed cells on these molecules for survival indicates that activation of a proenkephalin-dependent survival pathway during the transformation process has eventually led to downregulation of other survival molecules or pathways in an attempt by the cell to compensate for a maintained, inappropriate survival signal.

Example 3
Synthetic agents which bind the delta and kappa opioid receptors, or receptors related to them, induce apoptosis One explanation for the apoptotic effect of anti-proenkephalin antibodies is that proenkephalin and/or its proteolytic cleavage products are acting as ligands at receptors which promote cell survival; inhibition of such a receptor by competitive antagonists might therefore be predicted to promote apoptosis. It is possible that proenkephalin and/or its products are binding to receptors related or identical to known opioid receptor types. Enkephalin peptides are natural ligands for the delta opioid receptor, so the effects of an antagonist, naltrindole, which binds preferentially to the delta receptor, was investigated.

Induction of apoptosis by the opiate antagonist naltrindole
1) Effect of cell density HeLa cells were plated at low (approximately $0.5 \times 10^4$ per $cm^2$) and high (approximately $5 \times 10^4$ per $cm^2$) in medium containing 10% fetal calf serum (FCS) (to promote cell adherence); after 18 to 24 hours cells were washed to remove any adherent fetal calf serum, then challenged with drug at concentrations ranging from $10^{-4}M$ to $10^{-9}M$ in the presence of 0.1% (low) fetal calf serum (FCS). Naltrindole at $10^{-4}M$ administered to cells at low density and in low serum, induces apoptosis in 100% of cells within 1 to 2 hours. At higher cell densities, there is a slower entry into apoptosis so that it takes approximately 24 hours for the entire cell population to become apoptotic. Apoptosis is confirmed by time lapse imaging which reveals (short-lived) zeiotic blebbing followed by cell contraction and "rounding up"; by propidium iodide staining of fixed cells which reveals pyknotic and fragmented nuclei; lastly, by typical ultrastructural features. These results in HeLa cells have been reproduced many times.

Under conditions where apoptosis is slower or does not affect the entire cell population, upregulation of intracellular proenkephalin is seen after challenge with naltrindole (as in lowermost right hand panel FIG. 3). This may either reflect a specific feedback upregulation to opioid-like receptor antagonism, or a non-specific rescue attempt in sublethally damaged cells in the same way that proenkephalin responds to other sublethal injuries.

2) Effect at lower doses with repeated administration

There is a "steep" dose response so that little effect of naltrindole at $10^{-5}M$ is observed over a short time period; however, if this dose is repeated daily, there is evidence of DNA damage in the majority of cells on propidium iodide staining, and possibly greater amounts of apoptosis as well. This suggests that the cells are able to "rescue" themselves at low drug doses.

3) Protection from or enhancement of apoptosis with delta receptor agonists

Naltrindole at $10^{-4}M$ induces less apoptosis if co-administered to HeLa cells with a delta receptor agonist, DPDPE or DSLET, at $10^{-4}M$ in low serum. However; if cells are pre-treated with DPDPE at $10^{-4}M$ for one hour prior to administration of naltrindole, there is an accentuation of the apoptotic effect normally seen with naltrindole alone. Longer periods of pre-treatment with DPDPE have variable effects. This response would be consistent with a delta agonist at high dose causing paradoxical antagonism due to receptor internalisation. No effect is seen with delta agonists on their own, or with the mu agonist DAMGO alone or in combination.

4) Protection from apoptosis with serum-associated cytokines

If naltrindole is added in the presence of high (10%) FCS, the apoptotic effect is substantially less than in low serum. This suggests that survival cytokines present in fetal calf serum may 1) act as agonists at the same receptor(s); 2) upregulate a common intracellular survival pathway through signalling at different receptor(s); 3) downregulate a coupled death pathway (see later). Cytokines present in fetal calf serum which have an anti-apoptotic effect include PDGF, IGF-I, IGF-II, and insulin (Harrington et al. 1994 EMBO J., as earlier).

5) Inhibition of macromolecular synthesis enhances the apoptotic effect of naltrindole Co-administration of cycloheximide and naltrindole failed to rescue cells from apoptosis which indicates that the induction of apoptosis by naltrindole is not dependent on new protein synthesis. Cycloheximide alone induces apoptosis in HeLa cells which is consistent with the constitutive expression of death pathway molecules within these cells and their dependence on short half-life molecules for their survival.

6) Sensitisation to genotoxic injury in high serum

There is little effect of naltrindole at $10^{-4}M$, when cells are confluent and in high serum. However, an effect is seen at this drug dose under these conditions if cells have received a sublethal dose of ultraviolet radiation (such as 10 Joules per $m^2$) in addition. A greater amount of DNA damage is seen (nuclear fragmentation on propidium staining) than with UV alone; in addition non-fragmented nuclei show evidence of chromatin condensation, which would be consistent with inappropriate activation of a cdc2-related kinase. In this case, the activity of naltrindole is seen in the presence of high serum, which suggests that opioid-like receptor-mediated protection against genotoxic injury occurs even when exogenous survival factors are non-limiting.

Little effect of the non-selective opioid receptor antagonists naloxone and naltrexone, at doses from $10^{-9}M$ up to $10^{-3}M$ is seen even when HeLa cells are at low density and in low serum. Naltrexone at 10-3M indces transient zeiotic blebbing from which the cells seem to recover; there is some evidence of DNA damage with naloxone at $10^{-3}M$, but no overt evidence of apoptosis.

The dose of naltrindole required to achieve a biological effect in the above-described experiments is substantially higher than the inhibition constant of the drug for the cloned delta receptor expressed in COS cells (Yasuda et al., 1993 Proc. Natl. Acad. Sci. U.S.A. 90, 6736–6740) which is in the nanomolar range. However, these pharmacological values reflect competition between the agent and other ligands for binding sites on the cell membrane, and do not address a biological endpoint. One possible reason for the higher dose of naltrindole needed to achieve an apoptotic effect is that it is binding to a receptor which is related but not identical to the delta receptor. Another possibility, which may be an additional rather than alternative possibility, is that a delta-like receptor-mediated survival pathway is biologically coupled to an opposing pathway which mediates death. This could be an attempt by the cell to oppose the upregulation of a survival pathway which could confer an autonomous survival advantage to a cell, which would be dangerous for the reasons discussed earlier. Conversely, the cell could also compensate for inhibition of a survival pathway by down-regulation of a coupled death pathway. In this case, the kinetics of binding of an agent could become important. Thus, a high dose of drug may be needed to achieve rapid displacement of endogenous ligand so that antagonism of a delta-like receptor-mediated survival pathway has to be sufficiently swift to prevent compensatory downregulation of a coupled death pathway. It may also be that a receptor which promotes survival is physically coupled, in a heterodimeric complex, with a receptor which promotes death. Such complexing could affect the affinity of the receptor for its ligands.

The possibility that other opioid-like receptor types may promote death rather than survival would be one explanation for some preliminary data obtained by the applicant, that proenkephalin expressed in some cell systems appears to promote death rather than survival. The differential cleavage of proenkephalin has the potential to yield products which may bind to different classes of opioid receptors; for example, the product metorphamide predominantly binds mu receptors (Weber et al. 1983 Proc. Natl. Acad. Sci. U.S.A. 80, 7362–7366) whereas Met- and Leu-enkephalin are predominantly delta agonists. It is also possible that RNA from the same opioid receptor gene could be differentially spliced to yield products which promote death or survival. Primary transcripts from the bcl-2-related gene bcl-x can be differentially spliced to yield products which promote death or survival (Boise et al., 1993 Cell 74, 597–608) so there is some precedent for this. An identical primary translation product could also be differentially modified or complexed. Therefore, it is possible that different receptor types, or even the same receptor type, may promote death or survival.

Example 4

Induction of apoptosis with the opiate agonist U50488

HeLa cells were tested with a range of agonist drugs with preferences for one of the opioid receptor types. No apoptotic effect of the delta agonists DPDPE or DSLET is seen in the dose range $10^{-4}M$ to $10^{-9}M$; nor is there an apoptotic effect of the mu agonist DAMGO in the same dose range. In contrast, the kappa receptor agonist U50,488 has a marked apoptotic effect.

1) Effect of cell density and serum concentration

U50488 at $10^{-3}M$ administered to HeLa cells at low density and in low serum induces apoptosis in 100% of cells within ten to fifteen minutes; at $10^{-4}M$ apoptosis is induced in the entire population within one hour. Typical features of apoptosis are seen which include zeiotic blebbing, most evident on time lapse recording, and nuclear fragmentation on propidium idide staining of fixed cells. There are some subtle differences from apoptosis induced by naltrindole, such as more protracted zeiotic blebbing and more evidence of nuclear fragmentation. As with naltrindole, there is a much slower entry of the cell population into apoptosis at high cell densities, and some cells appear to be spared. High serum appears to protect HeLa cells to a greater extent from the effects of U50488 than from the effects of naltrindole.

As with naltrindole, U50488 at $10^{-5}M$ even in low serum at low density has little effect unless administered for longer periods with daily replenishment; again, there is evidence of DNA damage under these conditions.

2) Synergism between naltrindole and U50488

If U50488 and naltrindole, both at $10^{-4}M$ in low serum, are co-administered to cells at low density, an apoptotic effect in all cells within ten minutes rather than an hour is seen. If the drugs are co-administered at $10^{-5}M$, a possibly greater degree of DNA damage is seen but no overt increase in apoptosis, indicating that the steep dose response is maintained. There is no additional effect if naltrexone is co-administered with the two agents. These results suggest that death and survival pathways mediated through opioid-like receptors are coupled.

3) Apoptosis is induced in cells treated concurrently with sublethal doses of genotoxic agents and U50488

U50488 at $10^{-4}M$ administered to HeLa cells at high density in the presence of high serum had no apoptotic effect over a period of one to two hours. If U50488 at this dose is co-administered with etoposide at 50 or 100 $\mu M$ (N.B. micromolar) which again on its own is ineffective on dense cells at these doses over this time period, apoptosis was now induced in many cells. The apoptotic effect of the drug combination has been confirmed by time lapse imaging. Thus, the protective action of serum and high cell density against the apoptotic effect of U50488 is reduced by co-administration of a sublethal dose of a genotoxic agent.

4) Enhancement of the apoptotic effect of U50488 by cell cycle synchronisation

Administration of U50488 at $10^{-4}M$ to HeLa cells arrested in metaphase by pre-treatment with nocodazole at 100 ng/ml for 24 hours, induces apoptosis in nearly 100% of the cell population within 5 minutes; this effect is seen even when cells are at high density. Thus, the therapeutic effect of U50488, and therefore naltrindole also, will be enhanced by their administration following the induction of cell cycle arrest within the proliferating subpopulation of tumour cells.

Example 5

Antibody and synthetic agents preferentially induce apoptosis in tumour cells

Naltrindole and U50488 induced apoptosis in all cancer cell lines so far tested. These included HeLa (cervical carcinoma), MDA468 (breast carcinoma), A431 (vulval carcinoma), Hep-2 (head and neck squamous carcinoma), and the following ovarian carcinoma lines—CH1, SKOV—3, PXN94, A2780. In all cases, the effect of the drugs, if administered alone, is maximal on cells at low density in low serum. There are however, differing sensitivities and in some cases naltrindole appears more effective than U50488, and vice versa in others.

In general, the cancer lines listed above respond at least as well, and sometimes better, than HeLa cells. For example, the ovarian line CH1 appeared to be substantially more sensitive than HeLa cells to both drugs. When U50488 at a dose of 10-4M was administered to CH1 cells at low density and in low serum, apoptosis was induced in the entire population within 5 to 10 minutes; U50488 at 10-5M also has a clear apoptotic effect which is not evident in HeLa cells. When U50488 at 10-5M was co-administered with etoposide at 100 $\mu M$ (N.B. micromolar)to CH1 cells in high serum, apoptosis was induced in the entire cell population within 5 to 10 minutes. Etoposide at 100$\mu M$ (N.B. micromolar) on its own induced membrane ruffling and mild zeiotic blebbing only over a one to two hour time period. Thus, sublethal doses of U50488 and etoposide have a lethal effect when co-administered even when exogenous survival factors are non-limiting. Therefore it is believed that whereas the in vivo effect of U50488 on its own is likely to be dependent on the tumour environment, this is less likely to be the case if co-administered with genotoxic agents.

Naltrindole and U50488 were also tested against non-tumour cells in culture in order to estimate their likely toxicity against normal cells in vivo. MRC-5 cells (non-immortal human embryonic fibroblasts) at a late passage number did not undergo apoptosis upon challenge with U50488 or naltrindole, but did show evidence of chromatin condensation and/or DNA damage in all nuclei. In contrast, proliferating undifferentiated rodent myoblast cells (C2C12) readily underwent apoptosis with both compounds. C2C12 cells can be induced to differentiate in vitro. Under these conditions, as C2C12 cells become progressively more differentiated, there was increasing resistance to both drugs which has been confirmed by time lapse recording. Thus, it appears that U50488 and naltrindole will induce apoptosis in proliferating undifferentiated cell populations but not in differentiated cell populations.

Thus, tumour cells appear substantially more sensitive than non-proliferating, differentiated cells to both naltrindole and U50488.

Example 6

Overexpression of proenkephalin in the cell nucleus induces apoptotic death which is at least partly p53-dependent.

We have shown that proenkephalin exists in the nucleus in proliferating embryonic fibroblasts and myoblasts and is responsive to growth arrest and differentiation signals (Böttger and Spruce 1995). Removal of the hydrophobic signal peptide sequence by PCR mutagenesis (PEΔSS) or alteration of the normal ATG initiation codon to ATC (PE ATC) to force translation initiation from a downstream codon are sufficient to direct the product of transfected proenkephalin to the nucleus. Therefore, preventing access of proenkephalin to the secretory pathway is sufficient to confer at least a partial nuclear fate to the molecule (Bottger and Spruce 1995 J. Cell. Biol., 130, 1251–1262). The proenkephalin gene can undergo both alternate transcription initiation and alternate splicing of its primary transcript which would remove the exon encoding the signal peptide sequence; this therefore provides an in vivo precedent for the production of a primary translation product which lacks a signal peptide.

COS cells transiently transfected with mutated proenkephalin cDNAs tolerate nuclear overexpression of proenkephalin; nuclear localisation of the transfected gene product was confirmed in this and subsequent experiments using a p53 epitope tag. In contrast, when 3T3 cells are transiently transfected with the same constructs there are very few surviving transfected cells which appear apoptotic; in contrast, cells which overexpress proenkephalin targeted to the cytoplasm and secretory pathway (PE+SS) are viable.

Since p53 functions normally in 3T3 cells but is inactivated through SV40 large T antigen in COS cells, we explored the effect of nuclear overexpression of proenkephalin in C6 rodent fibroblasts which harbour a temperature sensitive P53 mutation (C6/ts p53 ). C6/ts cells transiently transfected with proenkephalin targeted to the nucleus as well as the cytoplasm show substantially reduced viability and have an apoptotic appearance at 32° C., the temperature at which p53 adopts a wild-type confirmation. However, at 37° C. many more cells survive which do not have an apoptotic appearance. Cells transiently transfected with PE+SS which is targeted to the cytoplasm and thence the secretory pathway are viable at both temperatures.

To confirm the apparent p53 dependence of death induced by nuclear overexpression of proenkephalin, stable C6/ts p53 lines were generated which overexpress proenkephalin targeted to the nucleus, or to the cytoplasm and secretory pathway. Lines which overexpress high levels of proenkephalin targeted to the nucleus show some apoptosis at 37° C. but apoptosis is substantially increased if the temperature of the cells is reduced to 32° to reactive p53. Thus, death induced by nuclear overexpression of proenkephalin is at least partly p53 dependent. Cells which are not overtly apoptotic at 37° C. show evidence of DNA damage such as micronuclei on propidium iodide staining; thus, we conclude that nuclear proenkephalin-mediated death is a result of DNA damage, which explains the dependence on p53.

Tumours which possess normal p53 function, which comprise approximately 50% of all human tumours, are therefore a particular target for the induction of apoptosis through a nuclear proenkephalin-dependent mechanism.

Since nuclear proenkephalin induces genetic damage, proenkephalin dysregulation in the nucleus will promote genetic damage as a result of environmental injury, whilst cytoplasmic proenkephalin will repress the suicide responce to this damage; inappropriate activation in the two pathways could therefore favour both the generation persistence of oncogenic mutations although this ought to be balanced by the proapoptotic effect of nuclear proenkephalin. If the DNA damage promotion and proapoptotic effects of proenkephalin are separable functions, the promotion of genetic damage through nuclear proenkephalin together with protection from suicide mediated through cytoplasmic proenkephalin could be potent early events in the oncogenic process.

Example 7

Effect of opiate-like receptor ligands on cells from the lens of the eye

The effect of naltrindole and U50488 on cells derived from the lens of the eye has been tested. These tests confirmed that these cells are dependent on proenkephalin for their survival. Primary cultures and continuous lines derived from the lens showed induction of apoptosis with both compounds but the timing of entry into apoptosis, monitored by time lapse recording, was slower compared to HeLa cells. Thus, naltrindole at $10^{-4}$M takes approximately 18 to 24 hours to show an apoptotic effect on low passage number cultures from bovine lens even in low serum. Lens cells generally were more resistant to U50488 than to naltrindole. High serum afforded protection against both compounds which indicates that receptors for exogenous survival factors are maintained in lens cells, despite their dependence in vivo on autocrine factors. Since the lens in vivo does not possess a blood or lymphatic supply, the activity of the compounds against lens cells would not represent a problem if the drugs were administered systemically, for example in tumour therapy. Furthermore, the induction of apoptosis by these compounds locally administered could be therapeutically useful, for example, as mentioned above, after surgical cataract removal, where the elimination of residual lens capsule cells is desirable to prevent future regrowth and opacification of the implant.

Example 8

Effect of other apoptosis-inducing agents or combination of agents on cells from the lens of the eye Cells of the rabbit lens cell line NN1003A when exposed to $10^{-4}$M U50488 in the absence of serum died by apoptosis within 24 hours. The same cells treated with $10^{-4}$M U50488 and $10^{-4}$M naltrindole in combination died within an hour. Primary bovine lens epithelial cells treated with $10^{-4}$M naltrindole died within 20 hours, while the same cells treated with a combination of $10^{-4}$M U50488 and $100\,\mu$M etoposide died within 24 hours. Both the rabbit cell line and the primary bovine cells increase the level of intracellular proenkephalin as judged by immunofluorescence microscopy in response to either serum starvation, etoposide, naltrindole and U50488. Naltrindole, U50488 and serum starvation all produced similar increases in cytoplasmic proenkephalin within 2 hours while etoposide took 24 hours to give the same level of staining.

We claim:

1. A method of inducing apoptosis in a cell comprising administering to said cell an agent able to modulate a biochemical pathway in said cell in which products of opioid peptide precursor genes participate in such a way as to induce the cell to apoptose.

2. A method according to claim 1 which said agent (i) neutralises proenkephalin or its proteolytic derivatives (ii) increases the level of nuclear proenkephalin and/or its derivatives or activates or mimics nuclear proenkephalin and/or its derivatives, (iii) acts as an antagonist at one or more receptors related or identical to the delta opioid receptor or (iv) acts as an agonist at one or more receptors related or identical to the kappa opioid receptor.

3. A method according to claim 2, said agent acting as an agonist at one or more receptors related or identical to the kappa opioid receptor and comprising trans-3,4-Dichloro-N-Methyl-N-(2-[1-pyrrolidinyl]cyclohexyl)benzene-acetamide(U-50488).

4. A method according to claim 2, said agent acting as an antagonist at one or more receptors related or identical to the delta opioid receptor and comprising 4,8 methanobenzofuro (2,3-a) pyrido (4,3-b) carbazole-1,8a(9H)-diol, 7-(cyclopropylmethyl)-5,6,7,8,14,14b-hexahydro.

5. A method according to claim 1 wherein said cell is any eye lens cell remaining after a cataract operation.

6. A method according to claim 5 wherein said agent is administered to said cell by being applied as a coating or adjunct to a replacement intraocular lens or to the anterior face of a lens implant following a cataract operation.

* * * * *

SEQUENCE LISTING

<160> NUMBER OF SEQ ID NOS: 11

<210> SEQ ID NO 1
<211> LENGTH: 102
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 1

Val Gln Leu Gln Glu Ser Gly Pro Glu Leu Val Lys Pro Gly Ala Ser
 1               5                  10                  15

Val Arg Ile Ser Cys Lys Thr Ser Gly Tyr Thr Phe Thr Glu Asn Thr
             20                  25                  30

Leu His Trp Val Lys Gln Ser His Gly Lys Ser Leu Glu Trp Ile Gly
         35                  40                  45

Gly Ile His Pro Lys Asn Gly Gly Thr Asn Tyr Asn Gln Lys Phe Lys
     50                  55                  60

Gly Lys Ala Thr Met Thr Val Asp Lys Ser Ser Ser Thr Ala Tyr Met
 65                  70                  75                  80

Asp Phe Arg Ser Leu Thr Phe Asp Ser Ala Val Tyr Tyr Cys Val
                 85                  90                  95

Arg Gly Asp Gly Ala Tyr
            100

<210> SEQ ID NO 2
<211> LENGTH: 6
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 2

Lys Arg Thr Leu Glu Ala
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 3

Arg Val Arg Leu Glu Ala
 1               5

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 4

Lys Lys Met Asn Asn Leu Tyr Val Leu Glu Leu Ser Glu Ala
 1               5                  10

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 5

Gln Lys Ile Asn Asn Arg Ser Gln Asp Pro Leu Ala Glu Val Ser Glu
 1               5                  10                  15

Phe Ala Val

<210> SEQ ID NO 6
<211> LENGTH: 109
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 6

Val Gln Leu Gln Glu Ser Gly Gly Leu Val Lys Pro Gly Gly Ser
 1               5                  10                  15

Leu Lys Leu Ser Cys Ala Ala Ser Gly Phe Thr Phe Ser Thr Tyr Ala
            20                  25                  30

Met Ser Trp Val Arg Gln Thr Pro Glu Lys Arg Leu Glu Trp Val Ala
        35                  40                  45

Thr Ile Ser Ser Gly Gly Ser Tyr Thr Tyr Tyr Pro Asp Ser Val Lys
    50                  55                  60

Gly Arg Phe Thr Ile Ser Arg Asp Asn Ala Lys Asn Thr Leu Tyr Leu
65                  70                  75                  80

Gln Met Ser Ser Leu Arg Ser Glu Asp Thr Ala Met Tyr Tyr Cys Ala
                85                  90                  95

Arg Leu Tyr Tyr Asp Tyr Asp Pro Tyr Val Met Asp Tyr
            100                 105

<210> SEQ ID NO 7
<211> LENGTH: 7
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 7

Lys Ser Ser Asn Met Val Phe
 1               5

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 8

```
Lys Phe Ser Cys Asn Val Ser Thr Ser Thr Ile Val Ser Gly Ala
 1               5                  10                  15
```

<210> SEQ ID NO 9
<211> LENGTH: 106
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 9

```
Val Gln Leu Gln Glu Ser Gly Thr Val Leu Ala Arg Pro Gly Ala Ser
 1               5                  10                  15

Val Lys Thr Ser Cys Lys Ala Ser Gly Tyr Ser Phe Thr Ser Tyr Trp
                20                  25                  30

Met His Trp Val Lys Gln Arg Pro Gly Gln Gly Leu Glu Trp Ile Gly
            35                  40                  45

Ala Ile Tyr Pro Gly Asn Ser Asp Thr Ser Tyr Asn Gln Lys Phe Lys
        50                  55                  60

Gly Lys Ala Lys Leu Thr Ala Val Thr Ser Ala Ser Thr Ala Tyr Met
 65                  70                  75                  80

Glu Leu Ser Ser Leu Thr Asn Glu Asp Ser Ala Val Tyr Tyr Cys Thr
                85                  90                  95

Arg Glu Gly Tyr Thr Thr Gly Gly Asp Tyr
                100                 105
```

<210> SEQ ID NO 10
<211> LENGTH: 105
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 10

```
Val Gln Leu Gln Glu Ser Gly Ala Glu Leu Val Lys Pro Gly Ala Ser
 1               5                  10                  15

Val Lys Leu Ser Cys Lys Ala Ser Gly Tyr Thr Phe Thr Arg Tyr Tyr
                20                  25                  30

Met Tyr Trp Val Lys Gln Arg Pro Gly Gln Gly Leu Glu Trp Ile Gly
            35                  40                  45

Glu Ile Asn Pro Ser Asn Gly Gly Thr Asn Phe Asn Glu Lys Phe Lys
        50                  55                  60

Ser Lys Ala Thr Leu Thr Val Asp Lys Ser Ser Ser Thr Ala Tyr Met
 65                  70                  75                  80

Gln Leu Ser Ser Leu Thr Ser Glu Asp Ser Ala Val Tyr Tyr Cys Thr
                85                  90                  95

Arg Gly Val Val Ala Ser Met Asp Tyr
                100             105
```

<210> SEQ ID NO 11
<211> LENGTH: 267
<212> TYPE: PRT
<213> ORGANISM: Artificial Sequence
<220> FEATURE:
<223> OTHER INFORMATION: Description of Artificial Sequence: sequence
      encoded by anti-proenkephalin immunoglobulin heavy
      chain variable domain genes

<400> SEQUENCE: 11

-continued

```
Met Ala Arg Phe Leu Thr Leu Cys Thr Trp Leu Leu Leu Leu Gly Pro
 1               5                  10                  15
Gly Leu Leu Ala Thr Val Arg Ala Glu Cys Ser Gln Asp Cys Ala Thr
             20                  25                  30
Cys Ser Tyr Arg Leu Val Arg Pro Ala Asp Ile Asn Phe Leu Ala Cys
             35                  40                  45
Val Met Glu Cys Glu Gly Lys Leu Pro Ser Leu Lys Ile Trp Glu Thr
         50                  55                  60
Cys Lys Glu Leu Leu Gln Leu Ser Lys Pro Glu Leu Pro Gln Asp Gly
 65                  70                  75                  80
Thr Ser Thr Leu Arg Glu Asn Ser Lys Pro Glu Glu Ser His Leu Leu
                 85                  90                  95
Ala Lys Arg Tyr Gly Gly Phe Met Lys Arg Tyr Gly Gly Phe Met Lys
             100                 105                 110
Lys Met Asp Glu Leu Tyr Pro Met Glu Pro Glu Glu Glu Ala Asn Gly
             115                 120                 125
Ser Glu Ile Leu Ala Lys Arg Tyr Gly Gly Phe Met Lys Lys Asp Ala
     130                 135                 140
Glu Glu Asp Asp Ser Leu Ala Asn Ser Ser Asp Leu Leu Lys Glu Leu
145                 150                 155                 160
Leu Glu Thr Gly Asp Asn Arg Glu Arg Ser His His Gln Asp Gly Ser
             165                 170                 175
Asp Asn Glu Glu Glu Val Ser Lys Arg Tyr Gly Gly Phe Met Arg Gly
             180                 185                 190
Leu Lys Arg Ser Pro Gln Leu Glu Asp Glu Ala Lys Glu Leu Gln Lys
         195                 200                 205
Arg Tyr Gly Gly Phe Met Arg Arg Val Gly Arg Pro Glu Trp Trp Met
     210                 215                 220
Asp Tyr Gln Lys Arg Tyr Gly Gly Phe Leu Lys Arg Phe Ala Glu Ala
225                 230                 235                 240
Leu Pro Ser Asp Glu Glu Gly Glu Ser Tyr Ser Lys Glu Val Pro Glu
             245                 250                 255
Met Glu Lys Arg Tyr Gly Gly Phe Met Arg Phe
             260                 265
```